US011810473B2

United States Patent
Wang et al.

(10) Patent No.: US 11,810,473 B2
(45) Date of Patent: Nov. 7, 2023

(54) OPTICAL SURFACE TRACKING FOR MEDICAL SIMULATION

(71) Applicant: SonoSim, Inc., Santa Monica, CA (US)

(72) Inventors: Matthew Wang, Los Angeles, CA (US); Kresimir Petrinec, Los Angeles, CA (US); Gabriele Nataneli, Beverly Hills, CA (US); Eric Savitsky, Malibu, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 437 days.

(21) Appl. No.: 16/776,348

(22) Filed: Jan. 29, 2020

(65) Prior Publication Data

US 2020/0242971 A1 Jul. 30, 2020

Related U.S. Application Data

(60) Provisional application No. 62/798,281, filed on Jan. 29, 2019.

(51) Int. Cl.
*G09B 23/28* (2006.01)
*G06T 7/73* (2017.01)
(Continued)

(52) U.S. Cl.
CPC .......... *G09B 23/286* (2013.01); *A61B 34/20* (2016.02); *A61B 90/36* (2016.02); *G06T 7/70* (2017.01);
(Continued)

(58) Field of Classification Search
CPC .. G06T 7/70; G06T 7/75; G06V 20/64; G06V 20/95
See application file for complete search history.

(56) References Cited

U.S. PATENT DOCUMENTS

| 1,488,233 A | 3/1924 | Diehl |
| 1,762,937 A | 6/1930 | Staud |

(Continued)

FOREIGN PATENT DOCUMENTS

| EP | 1103223 A2 | 5/2001 |
| EP | 2801966 A1 | 11/2014 |

(Continued)

OTHER PUBLICATIONS

English version of JP-2011097238-A (Year: 2011).*
(Continued)

*Primary Examiner* — Grace Q Li
(74) *Attorney, Agent, or Firm* — Cislo & Thomas, LLP

(57) ABSTRACT

A system and method of training how to use a medical device using an instrument such as a mock ultrasound probe or syringe to be tracked in 3D space with six degrees of freedom using an internal optical camera, a light source (e.g. infrared LEDs), and a display of markers arranged on a surface. By extracting corner information for each marker, a 3D transformation can be established, allowing the system to know the instrument's position and orientation in 3D space relative to that marker. Each marker also encodes a numerical value corresponding to its predetermined position and orientation on the surface, allowing the instrument to determine its own position and orientation relative to the surface. Thus, as long as the instrument is able to see at least one marker on an optical surface, the system will know its full 3D position and orientation relative to the whole optical surface.

1 Claim, 18 Drawing Sheets

(51) Int. Cl.
  *G06T 7/70*   (2017.01)
  *G06V 20/64*  (2022.01)
  *G06V 20/00*  (2022.01)
  *A61B 90/00*  (2016.01)
  *A61B 34/20*  (2016.01)

(52) U.S. Cl.
  CPC .............. *G06T 7/75* (2017.01); *G06V 20/64*
      (2022.01); *G06V 20/95* (2022.01); *A61B*
      *2034/2055* (2016.02); *A61B 2090/367*
      (2016.02); *G06T 2207/10028* (2013.01)

(56) References Cited

U.S. PATENT DOCUMENTS

| | | |
|---|---|---|
| 2,019,121 A | 10/1935 | De Rewal |
| 2,112,019 A | 3/1938 | Gyger |
| 2,127,610 A | 8/1938 | Moore |
| 2,705,049 A | 3/1955 | Brooks |
| 2,705,307 A | 3/1955 | Edson |
| 2,722,947 A | 11/1955 | Sragal |
| 2,886,316 A | 5/1959 | Ayala |
| 4,040,171 A | 8/1977 | Cline et al. |
| 4,838,863 A | 6/1989 | Allard et al. |
| 4,838,869 A | 6/1989 | Allard |
| 4,994,034 A | 2/1991 | Botich et al. |
| 5,231,381 A | 7/1993 | Duwaer |
| 5,513,992 A | 5/1996 | Refait |
| 5,609,485 A | 3/1997 | Bergman et al. |
| 5,678,565 A | 10/1997 | Sarvazyan |
| 5,689,443 A | 11/1997 | Ramanathan |
| 5,701,900 A | 12/1997 | Shehada et al. |
| 5,704,791 A | 1/1998 | Gillio |
| 5,755,577 A | 5/1998 | Gillio |
| 5,767,839 A | 6/1998 | Rosenberg |
| 5,776,062 A | 7/1998 | Nields |
| 5,791,908 A | 8/1998 | Gillio |
| 5,800,177 A | 9/1998 | Gillio |
| 5,800,178 A | 9/1998 | Gillio |
| 5,800,179 A | 9/1998 | Bailey |
| 5,800,350 A | 9/1998 | Coppleson et al. |
| 5,827,942 A | 10/1998 | Madsen et al. |
| 5,882,206 A | 3/1999 | Gillio |
| 5,889,237 A | 3/1999 | Makinwa |
| 5,934,288 A | 8/1999 | Avila et al. |
| 6,001,472 A | 12/1999 | Ikeda et al. |
| 6,048,312 A | 4/2000 | Ishrak et al. |
| 6,063,030 A | 5/2000 | Vara et al. |
| 6,068,597 A | 5/2000 | Lin |
| 6,074,213 A | 6/2000 | Hon |
| 6,113,395 A | 9/2000 | Hon |
| 6,117,078 A | 9/2000 | Lysyansky et al. |
| 6,119,033 A | 9/2000 | Spigelman et al. |
| 6,122,538 A | 9/2000 | Sliwa, Jr. et al. |
| 6,156,213 A | 12/2000 | Dudley et al. |
| 6,193,657 B1 | 2/2001 | Drapkin |
| 6,267,599 B1 | 7/2001 | Bailey |
| 6,468,212 B1 | 10/2002 | Scott et al. |
| 6,502,756 B1 | 1/2003 | Fåhraeus |
| 6,511,427 B1 | 1/2003 | Sliwa, Jr. et al. |
| 6,548,768 B1 | 4/2003 | Pettersson et al. |
| 6,570,104 B1 | 5/2003 | Ericson et al. |
| 6,654,000 B2 | 11/2003 | Rosenberg |
| 6,663,008 B1 | 12/2003 | Pettersson et al. |
| 6,665,554 B1 | 12/2003 | Charles et al. |
| 6,666,376 B1 | 12/2003 | Ericson |
| 6,667,695 B2 | 12/2003 | Pettersson et al. |
| 6,674,427 B1 | 1/2004 | Pettersson et al. |
| 6,689,966 B2 | 2/2004 | Wiebe |
| 6,693,626 B1 | 2/2004 | Rosenberg |
| 6,694,163 B1 | 2/2004 | Vining |
| 6,698,660 B2 | 3/2004 | Fåhraeus et al. |
| 6,714,213 B1 | 3/2004 | Lithicum et al. |
| 6,714,901 B1 | 3/2004 | Cotin et al. |
| 6,719,470 B2 | 4/2004 | Berhin |
| 6,722,574 B2 | 4/2004 | Skantze et al. |
| 6,732,927 B2 | 5/2004 | Olsson et al. |
| 6,750,877 B2 | 6/2004 | Rosenberg et al. |
| 6,780,016 B1 | 8/2004 | Toly |
| 6,816,148 B2 | 11/2004 | Mallett et al. |
| 6,836,555 B2 | 12/2004 | Ericson et al. |
| 6,854,821 B2 | 2/2005 | Ericson et al. |
| 6,864,880 B2 | 3/2005 | Hugosson et al. |
| 6,878,062 B2 | 4/2005 | Bjorklund et al. |
| 6,896,650 B2 | 5/2005 | Tracey et al. |
| 6,916,283 B2 | 7/2005 | Tracey et al. |
| 6,927,916 B2 | 8/2005 | Craven-Bartle |
| 6,929,183 B2 | 8/2005 | Pettersson |
| 6,929,481 B1 | 8/2005 | Alexander et al. |
| 6,947,033 B2 | 9/2005 | Fåhraeus et al. |
| 6,958,747 B2 | 10/2005 | Sahlberg et al. |
| 6,966,495 B2 | 11/2005 | Lynggaard et al. |
| 6,992,655 B2 | 1/2006 | Ericson et al. |
| 7,002,559 B2 | 2/2006 | Ericson |
| 7,035,429 B2 | 4/2006 | Andreasson |
| 7,037,258 B2 | 5/2006 | Chatenever et al. |
| 7,050,653 B2 | 5/2006 | Edso et al. |
| 7,054,487 B2 | 5/2006 | Ericson et al. |
| 7,072,529 B2 | 7/2006 | Hugosson et al. |
| 7,089,308 B2 | 8/2006 | Fransson et al. |
| 7,094,977 B2 | 8/2006 | Ericson et al. |
| 7,110,604 B2 | 9/2006 | Olsson |
| 7,120,320 B2 | 10/2006 | Petterson et al. |
| 7,121,465 B2 | 10/2006 | Rignell |
| 7,127,682 B2 | 10/2006 | Sandstrom et al. |
| 7,143,952 B2 | 12/2006 | Ericson |
| 7,145,556 B2 | 12/2006 | Pettersson |
| 7,154,056 B2 | 12/2006 | Bergqvist et al. |
| 7,162,087 B2 | 1/2007 | Bryborn |
| 7,167,164 B2 | 1/2007 | Ericson et al. |
| 7,172,131 B2 | 2/2007 | Pettersson et al. |
| 7,175,095 B2 | 2/2007 | Pettersson et al. |
| 7,176,896 B1 | 2/2007 | Fahraeus et al. |
| 7,180,509 B2 | 2/2007 | Fermgard et al. |
| 7,195,166 B2 | 3/2007 | Olsson et al. |
| 7,202,861 B2 | 4/2007 | Lynggaard |
| 7,202,963 B2 | 4/2007 | Wiebe et al. |
| 7,239,306 B2 | 7/2007 | Fahraeus et al. |
| 7,246,321 B2 | 7/2007 | Bryborn et al. |
| 7,248,250 B2 | 7/2007 | Pettersson et al. |
| 7,249,256 B2 | 7/2007 | Hansen et al. |
| 7,249,716 B2 | 7/2007 | Bryborn |
| 7,254,839 B2 | 8/2007 | Fahraeus et al. |
| 7,278,017 B2 | 10/2007 | Skantze |
| 7,281,668 B2 | 10/2007 | Pettersson et al. |
| 7,283,676 B2 | 10/2007 | Olsson |
| 7,293,697 B2 | 11/2007 | Wiebe et al. |
| 7,295,193 B2 | 11/2007 | Fahraeus |
| 7,296,075 B2 | 11/2007 | Lynggaard |
| 7,321,692 B2 | 1/2008 | Bryborn et al. |
| 7,333,947 B2 | 2/2008 | Wiebe et al. |
| 7,345,673 B2 | 3/2008 | Ericson et al. |
| 7,353,393 B2 | 4/2008 | Hansen et al. |
| 7,356,012 B2 | 4/2008 | Wiebe et al. |
| 7,371,068 B2 | 5/2008 | Lloyd et al. |
| 7,382,361 B2 | 6/2008 | Burstrom et al. |
| 7,385,595 B2 | 6/2008 | Bryborn et al. |
| 7,408,536 B2 | 8/2008 | Hugosson et al. |
| 7,415,501 B2 | 8/2008 | Burstrom |
| 7,418,160 B2 | 8/2008 | Lynggaard |
| 7,422,154 B2 | 9/2008 | Ericson |
| 7,441,183 B2 | 10/2008 | Burstrom et al. |
| 7,457,413 B2 | 11/2008 | Thuvesholmen et al. |
| 7,457,476 B2 | 11/2008 | Olsson |
| 7,543,753 B2 | 6/2009 | Pettersson |
| 7,588,191 B2 | 9/2009 | Pettersson et al. |
| 7,600,693 B2 | 10/2009 | Pettersson |
| 7,649,637 B2 | 1/2010 | Wiebe et al. |
| 7,670,070 B2 | 3/2010 | Craven-Bartle |
| 7,672,513 B2 | 3/2010 | Bjorklund et al. |
| 7,701,446 B2 | 4/2010 | Sahlberg et al. |
| 7,710,408 B2 | 5/2010 | Ericson |
| 7,751,089 B2 | 7/2010 | Fahraeus et al. |
| 7,753,283 B2 | 7/2010 | Lynggaard |
| 7,777,777 B2 | 8/2010 | Bowman et al. |

(56) References Cited

U.S. PATENT DOCUMENTS

| | | |
|---|---|---|
| 7,788,315 B2 | 8/2010 | Johansson |
| 7,794,388 B2 | 9/2010 | Draxinger et al. |
| 7,806,696 B2 | 10/2010 | Alexander et al. |
| 7,833,018 B2 | 11/2010 | Alexander et al. |
| 7,845,560 B2 | 12/2010 | Emanuel et al. |
| 7,850,454 B2 | 12/2010 | Toly |
| 7,857,626 B2 | 12/2010 | Toly |
| 7,871,850 B2 | 1/2011 | Park |
| 7,931,470 B2 | 4/2011 | Alexander et al. |
| 8,116,549 B2 | 2/2012 | Warmath et al. |
| 8,244,506 B2 | 8/2012 | Butsev et al. |
| 8,294,972 B2 | 10/2012 | Chung |
| 8,428,326 B2 | 4/2013 | Falk et al. |
| 8,480,404 B2 | 7/2013 | Savitsky |
| 8,480,406 B2 | 7/2013 | Alexander et al. |
| 8,721,344 B2 | 5/2014 | Marmaropoulos et al. |
| 9,128,116 B2 | 9/2015 | Welch et al. |
| 9,171,484 B2 | 10/2015 | Fitzli et al. |
| 9,251,721 B2 | 2/2016 | Lampotang |
| 9,436,993 B1 * | 9/2016 | Stolka ............... G06T 7/11 |
| 9,626,805 B2 | 4/2017 | Lampotang et al. |
| 9,792,836 B2 | 10/2017 | Rios et al. |
| 9,870,721 B2 | 1/2018 | Savitsky et al. |
| 9,918,657 B2 | 3/2018 | Daon et al. |
| 10,052,010 B2 | 8/2018 | Feddema |
| 10,132,015 B2 | 11/2018 | Woodruff et al. |
| 11,011,077 B2 | 5/2021 | Garcia Kilroy |
| 2001/0031920 A1 | 10/2001 | Kaufman et al. |
| 2002/0076581 A1 | 6/2002 | McCoy |
| 2002/0076681 A1 | 6/2002 | Leight et al. |
| 2002/0088926 A1 | 7/2002 | Prasser |
| 2002/0099310 A1 | 7/2002 | Kimchy et al. |
| 2002/0168618 A1 | 11/2002 | Anderson et al. |
| 2002/0173721 A1 | 11/2002 | Grunwald et al. |
| 2003/0210812 A1 | 11/2003 | Khamene et al. |
| 2004/0043368 A1 | 3/2004 | Hsieh et al. |
| 2004/0087850 A1 | 5/2004 | Okerlund et al. |
| 2005/0084833 A1 | 4/2005 | Lacey et al. |
| 2005/0119569 A1 | 6/2005 | Ohtake |
| 2005/0181342 A1 | 8/2005 | Toly |
| 2005/0214726 A1 | 9/2005 | Feygin et al. |
| 2005/0228617 A1 | 10/2005 | Kerwin et al. |
| 2005/0283075 A1 | 12/2005 | Ma et al. |
| 2006/0020204 A1 | 1/2006 | Serra et al. |
| 2006/0098010 A1 | 5/2006 | Dwyer et al. |
| 2007/0088213 A1 | 4/2007 | Poland |
| 2007/0161904 A1 | 7/2007 | Urbano |
| 2007/0232907 A1 | 10/2007 | Pelissier et al. |
| 2007/0236514 A1 | 10/2007 | Augusanto |
| 2007/0238085 A1 | 10/2007 | Colvin et al. |
| 2008/0009743 A1 | 1/2008 | Hayasaka |
| 2008/0137071 A1 | 6/2008 | Chow |
| 2008/0187896 A1 | 8/2008 | Savitsky |
| 2008/0200807 A1 | 8/2008 | Wright et al. |
| 2008/0204004 A1 | 8/2008 | Anderson |
| 2008/0269606 A1 | 10/2008 | Matsumura |
| 2008/0294096 A1 | 11/2008 | Uber et al. |
| 2008/0312884 A1 | 12/2008 | Hostettler et al. |
| 2009/0006419 A1 | 1/2009 | Savitsky |
| 2009/0043195 A1 | 2/2009 | Poland |
| 2009/0046912 A1 | 2/2009 | Hostettler |
| 2009/0130642 A1 | 5/2009 | Tada et al. |
| 2009/0209859 A1 | 8/2009 | Tsujita et al. |
| 2009/0266957 A1 | 10/2009 | Cermak |
| 2009/0305213 A1 | 12/2009 | Burgkart et al. |
| 2009/0311655 A1 | 12/2009 | Karkanias et al. |
| 2010/0055657 A1 | 3/2010 | Goble et al. |
| 2010/0104162 A1 | 4/2010 | Falk et al. |
| 2010/0179428 A1 | 7/2010 | Pedersen et al. |
| 2010/0268067 A1 | 10/2010 | Razzaque et al. |
| 2010/0277422 A1 | 11/2010 | Muresianu et al. |
| 2011/0010023 A1 * | 1/2011 | Kunzig ............... G05D 1/0291 701/2 |
| 2011/0306025 A1 | 12/2011 | Sheehan et al. |
| 2012/0021993 A1 | 1/2012 | Kim et al. |
| 2012/0058457 A1 | 3/2012 | Savitsky |
| 2012/0143142 A1 | 6/2012 | Klein |
| 2012/0150797 A1 | 6/2012 | Landy et al. |
| 2012/0179039 A1 | 7/2012 | Pelissier et al. |
| 2012/0200977 A1 | 8/2012 | Nestler |
| 2012/0219937 A1 | 8/2012 | Hughes et al. |
| 2012/0237102 A1 | 9/2012 | Savitsky et al. |
| 2012/0237913 A1 | 9/2012 | Savitsky et al. |
| 2012/0238875 A1 | 9/2012 | Savitsky et al. |
| 2012/0251991 A1 | 10/2012 | Savitsky et al. |
| 2013/0046523 A1 | 2/2013 | Van Dinther |
| 2013/0064036 A1 | 3/2013 | Lee et al. |
| 2013/0065211 A1 | 3/2013 | Amso et al. |
| 2013/0158411 A1 | 6/2013 | Miyasaka |
| 2013/0179306 A1 | 7/2013 | Want et al. |
| 2013/0236872 A1 | 9/2013 | Laurusonis et al. |
| 2013/0267838 A1 | 10/2013 | Fronk et al. |
| 2014/0087347 A1 | 3/2014 | Tracy |
| 2014/0114194 A1 | 4/2014 | Kanayama et al. |
| 2014/0119645 A1 * | 5/2014 | Zimet-Rubner ...... G06F 3/0304 382/165 |
| 2014/0120505 A1 | 5/2014 | Rios et al. |
| 2014/0170620 A1 | 6/2014 | Savitsky et al. |
| 2014/0228685 A1 | 8/2014 | Eelbode |
| 2014/0272878 A1 | 9/2014 | Shim et al. |
| 2015/0056591 A1 | 2/2015 | Tepper et al. |
| 2015/0078639 A1 | 3/2015 | Hausotte |
| 2015/0084897 A1 | 3/2015 | Nataneli et al. |
| 2015/0086955 A1 | 3/2015 | Poniatowski et al. |
| 2015/0086956 A1 | 3/2015 | Savitsky et al. |
| 2015/0140538 A1 | 5/2015 | Savitsky et al. |
| 2015/0154890 A1 | 6/2015 | Savitsky et al. |
| 2015/0190112 A1 | 7/2015 | Yeo et al. |
| 2015/0213731 A1 | 7/2015 | Sato |
| 2016/0104393 A1 | 4/2016 | Savitsky et al. |
| 2016/0133158 A1 | 5/2016 | Sui et al. |
| 2016/0259424 A1 | 9/2016 | Nataneli et al. |
| 2016/0284240 A1 | 9/2016 | Liang |
| 2016/0314715 A1 | 10/2016 | Savitsky et al. |
| 2016/0314716 A1 | 10/2016 | Grubbs |
| 2016/0328998 A1 | 11/2016 | Pedersen et al. |
| 2017/0018204 A1 | 1/2017 | Savitsky et al. |
| 2017/0028141 A1 | 2/2017 | Fiedler et al. |
| 2017/0035517 A1 | 2/2017 | Geri |
| 2017/0046985 A1 | 2/2017 | Hendrickson et al. |
| 2017/0110032 A1 | 4/2017 | O'Brien et al. |
| 2017/0200399 A1 | 7/2017 | Thomas et al. |
| 2017/0270829 A1 | 9/2017 | Bauss |
| 2017/0352294 A1 | 12/2017 | Nataneli et al. |
| 2017/0352295 A1 | 12/2017 | Belzacq et al. |
| 2017/0372640 A1 | 12/2017 | Lampotang et al. |
| 2018/0049622 A1 | 2/2018 | Ryan et al. |
| 2018/0071032 A1 | 3/2018 | de Almeida Barreto |
| 2018/0137784 A1 | 5/2018 | Savitsky et al. |
| 2018/0197441 A1 | 7/2018 | Rios et al. |
| 2018/0211563 A1 | 7/2018 | Savitsky et al. |
| 2018/0225992 A1 | 8/2018 | Gonsalves et al. |
| 2018/0330635 A1 | 11/2018 | Savitsky et al. |
| 2018/0366034 A1 | 12/2018 | Casals Gelpi |
| 2019/0057620 A1 | 2/2019 | Eggert |
| 2019/0231436 A1 | 8/2019 | Panse |
| 2019/0321657 A1 * | 10/2019 | Hale ................... H04N 13/246 |
| 2019/0371204 A1 | 12/2019 | Savitsky et al. |
| 2020/0126449 A1 | 4/2020 | Horst |
| 2020/0138518 A1 * | 5/2020 | Lang ...................... A61B 5/05 |
| 2020/0242954 A1 | 7/2020 | Wang et al. |
| 2020/0242972 A1 | 7/2020 | Petrinec et al. |
| 2021/0128125 A1 * | 5/2021 | Sitti ................ A61B 1/00158 |
| 2021/0134186 A1 | 5/2021 | Savitsky et al. |
| 2021/0186311 A1 * | 6/2021 | Levy ................ A61B 1/00114 |

FOREIGN PATENT DOCUMENTS

| | | |
|---|---|---|
| JP | 2011097238 A * | 5/2011 |
| RU | 2127610 C1 | 3/1999 |
| RU | 1994040171 | 11/2014 |
| WO | 2006060406 A1 | 6/2006 |
| WO | WO 2009/003664 | 1/2009 |

(56) References Cited

FOREIGN PATENT DOCUMENTS

| | | |
|---|---|---|
| WO | WO 2013/140315 | 9/2013 |
| WO | PCT/US2013/058661 | 3/2014 |
| WO | WO 2017/098036 | 6/2017 |

OTHER PUBLICATIONS

Chung, Gregory, "Effects of Simulation-Based Practice on Focused Assessment . . . ", Military Medicine, Oct. 2013, vol. 178.

Aligned Management Associates, Inc., Corporate home page describing organizing committee, overview, Procedicus MIST[trademark]-suturing module 30.0, 6 pgs., obtained from website Sep. 6, 2004.

American Academy of Emergency Medicine, conference: 11th annual scientific assembly preconference ultrasound courts, http://www.aaem.org/education/scientificassembly/sa05/precon/ultrasound.shtml, 6 pgs, obtained from website Feb. 16, 2005.

Barbosa, J. et. al., "Computer education in emergency medicine residency programs," http://www.med-ed-online.org/res00002.htm, 8 pgs, obtained from website Sep. 6, 2004.

Brannam, Let al, "Emergency nurses utilization of ultrasound guidance for placement of peripheral intravenous lines in difficult-access patients," Acad Emerg Med, 11(12):1361-1363, Dec. 2004.

Calvert, N. et al., "The effectiveness and cost-effectiveness of ultrasound locating devices for central venous access: a systematic review and economic evaluation/executive summary," Health Tech Assess 2003, 7(12), 4 pgs.

Center for Human Simulation, corporate home page describing overview/people, http://www.uchsc.edu, 7 pgs, obtained from website Sep. 6, 2004.

CIMIT News, "The medical access program: new CIMIT initiative to benefit underserved patients/partners telemedicine and CIMIT launch new initiative: stay connected, be healthy/highlights: operating room of the future plug- and-play project," http://www.cimit.org, Jan. 2005; Vol11(2), 2 pgs., obtained from website Mar. 1, 2005.

Colt, H. G. et. al., "Virtual reality bronchoscopy simulation: a revolution in procedural training," Chest 2001; 120:1333-1339.

Computer Motion, "About computer motion: technology to enhance surgeons capabilities, improve patient outcomes and reduce healthcare costs/corporate alliances/products solutions for surgical innovation/training on the da Vinci[registered] surgical system-introduction," 2002 Computer Motion, http://www.computermotion.com, 6 pgs.

Delp, Setal, "Surgical simulation—an emerging technology for training in emergency medicine," Presence, 6(2):147-159, Apr. 1997 (abstract).

Dorner, R. et. al., "Synergies between interactive training simulations and digital storytelling: a component-based framework," Computer Graphics, 26(1):45-55, Feb. 2002 (abstract).

Duque, D. and Kessler S., "Ultrasound guided vascular access," Amer Coli Emerg Phy., http://www.nyacep.org/education/articles/ultrasound%20vascular%20access.htm, 2 pgs, obtained from website May 11, 2005.

Espinet, A. and Dunning J., "Does ultrasound-guided central line insertion reduce complications and time to placement in elective patients undergoing cardiac surgery," Inter Cardiovascular Thoracic Surg, 3:523-527, 2004; http://licvts.ctsnetjournals.org/cgi/content/full/3/3/523, 6 pgs, obtained from website May 11, 2005 (abstract).

Gallagher, A. G. et al., "Virtual reality training for the operating room and cardiac catheterization laboratory," Lancet, 364:1538-1540, Oct. 23, 2004.

Gallagher, A. G. et al., "Psychomotor skills assessment in practicing surgeons experienced in performing advanced laparoscopic procedures," AM Coll Surg, 197(3):479-488, Sep. 2003.

Gausche, M. et. al., "Effect on out-of-hospital pediatric endotracheal intubation on survival and neurological outcome: a controlled clinical trial," JAMA, 283(6):783-790, Feb. 9, 2000.

Gore, D. C. and Gregory, S. R., "Historical perspective on medical errors: Richard Cabot and the Institute of Medicine," J Amer Coll Surg, 197(4), 5 pgs, Oct. 2003.

Grantcharov, T. P. et. al., "Randomized clinical trial of virtual reality simulation for laparoscopic skills training," Br J Surg, 91(2):146-150, Feb. 1, 2004 (abstract).

Grantcharov, T. P. et. al., "Learning curves and impact of previous operative experience on performance on a virtual reality simulator to test laparoscopic surgical skills," Am J Surg, 185(2):146-149, Feb. 1, 2004 (abstract).

Haluck, R. S., et al., "Are surgery training programs ready for virtual reality A survey of program directors in general surgery," Arch Surg, 135(7):786-792, Jul. 1, 2000.

Helmreich, R. L., "On error management: lessons from aviation," BMJ, 320:781-785, Mar. 2000.

Huckman, R. S. and Pisano, G. P., "Turf battles in coronary revascularization," N Engl J Med, http://www.nejm.org, 4 pgs, 352(9):857-859, Mar. 3, 2005.

Immersion Corporation, URL: http://www.immersion.com/corporate/products/, corporate home page describing Immersions surgical training simulators—"Wireless Data Glove: The CyberGiove[registered]II System," 5 pgs, obtained from the website Nov. 17, 2005 and Jan. 24, 2008.

Injuryboard.com, "Reducing complications associated with central vein catheterization," URSL: http://www.injuryboard.com/view.cfm/Article=668, 5 pgs, obtained from website May 11, 2005.

Intersense, home page listing motion tracking products, http://www.isense.com/prodcuts.aspxid=42, 1 pg, obtained from website Jan. 24, 2008.

Jemmett, M. E., et. al., "Unrecognized misplacement of endotracheal tubes in a mixed urban to rural emergency medical services setting," Acad Emerg Med, 10(9):961-964, Sep. 2003.

Katz, S. H. and Falk, J. L., "Misplaced endotrachial tubes by paramedics in an urban medical services system," Annals Emerg Med, 37:32-37, Jan. 2001.

Lewis, R., "Educational research: time to reach the bar, not lower it," Acad Emerg Med, 12(3):247-248, Mar. 2005.

Liu, A. et al., "A survey of surgical simulation: applications, technology, and education," Presence, 12(6):1-45, Dec. 2003.

Manchester Visulations Centre, "Webset project-bringing 3D medical training tools to the WWW," http://www.sve.man.ac.uklmvc/research/previous/website, 3 pgs, obtained from the website Sep. 8, 2004.

McLellan, H., "Virtual realities," McLellan Wyatt Digital, 33 pgs.

Medical Simulation Corporation, corporate home page describing management team/frequently asked questions, http://www.medsimulation.com/about_msc/key_employees.asp, 7 pgs, obtained from website Nov. 25, 2004.

Medtronic, "The StealthStation[registered] treatment guidance system," the corporate home page describing the company fact sheet and profile; http://www.medtronic.com/Newsroom, 4 pgs, obtained from website Mar. 5, 2005.

Mort, T. C., "Emergency tracheal intubation: complications associated with repeated laryngoscopic attempts," Anesth Analg, 99(2):607-613, Aug. 2004, 1 pg, obtained from website Sep. 8, 2004 (abstract).

Nazeer, S. R., et. al., "Ultrasound-assisted paracentesis performed by emergency physicians v.s. the traditional technique: a prospective, randomized study," Amer J of Emer Med, 23:363-367, 2005.

NCA Medical Simulation Center, Tutorial-simulation for medical training, http://Simcen.usuhs.millmiccaie, 4 pgs, 2003.

Next Dimension Imaging, "Products-Anatomy Analyzer 2," http://www.nexted.com/anatomyanalyzer.asp, 2 pgs, obtained from website Dec. 7, 2004.

Norris, T. E. et. al., "Teaching procedural skills," J General Internal Med, 12(S2):S64-S70, Apr. 1997.

On the Net Resources-Education and Training, URL: http://www.hitl.washington.edu/projects/knowledge_base/education.html, corporate home page regarding internet sites regarding education and training, 16 pgs, obtained from website Jan. 8, 2005.

Osberg, K. M., "Virtual reality and education: a look at both sides of the sword," http://www.hitl.washington.edu/publications/r-93-7/, 19 pgs, Dec. 14, 1992, obtained from website Jan. 21, 2008.

Osmon, S. et. al., "Clinical investigations: reporting of medical errors: an intensive care unit experience," Grit Care Med, 32(3), 13 pgs, Mar. 2004.

(56) References Cited

OTHER PUBLICATIONS

Ponder, M., et. al., "Immersive VR decision training: telling interactive stories featuring advanced human simulation technologies," Eurographics Association 2003, 10 pgs.

Primal, corporate home page describing resources for teaching healthcare practitioners, 2 pgs, obtained from website.

Prystowsky, J. B. et. al., "A virtual reality module for intravenous catheter placement," Am J Surg 1999; 177(2):171-175 (abstract).

Reachin, "Medical Training Development Centre/Reachin technologies AB has entered into a corporation with Mentice AB," Jan. 20, 2004, 4 pgs, obtained from website Nov. 9, 2004.

Rothschild, J. M., "Ultrasound guidance of central vein catheterization," NCBI, Nat Lib Med, www.ncbi.nlm.nih.gov/books/, HSTAT 21, 6 pgs, obtained from website May 11, 2005.

Rowe, R. and Cohen, R. A., "An evaluation of a virtual reality airway simulator," Anesth Analg 2002, 95:62-66.

Sensable Technologies, "PHANTOM Omni Haptic Device," 2 pgs, http://www.sensable.com/haptic-ohantom-omni.htm., obtained from website Jan. 24, 2008.

Shaffer, K., "Becoming a physician: teaching anatomy in a digital age," NEJM, Sep. 23, 2004; 351(13):1279-81 (extract of first 100 words—No abstract).

Garrido-Jurado et al., Automatic generation and detection of highly reliable fiducial markers under occlusion, 2014, Pattern Recognition.

Healthcare Solutions, 3D Systems, Pelvic Mentor, 3 pages.

Sonocubic Fine, "A Revolution in Obstetrical Ultrasound," 1 page.

Medge Platforms, Inc., "Volutracer O.P.U.S. Optical Positioning Ultrasound Simulator," 2 pages.

\* cited by examiner

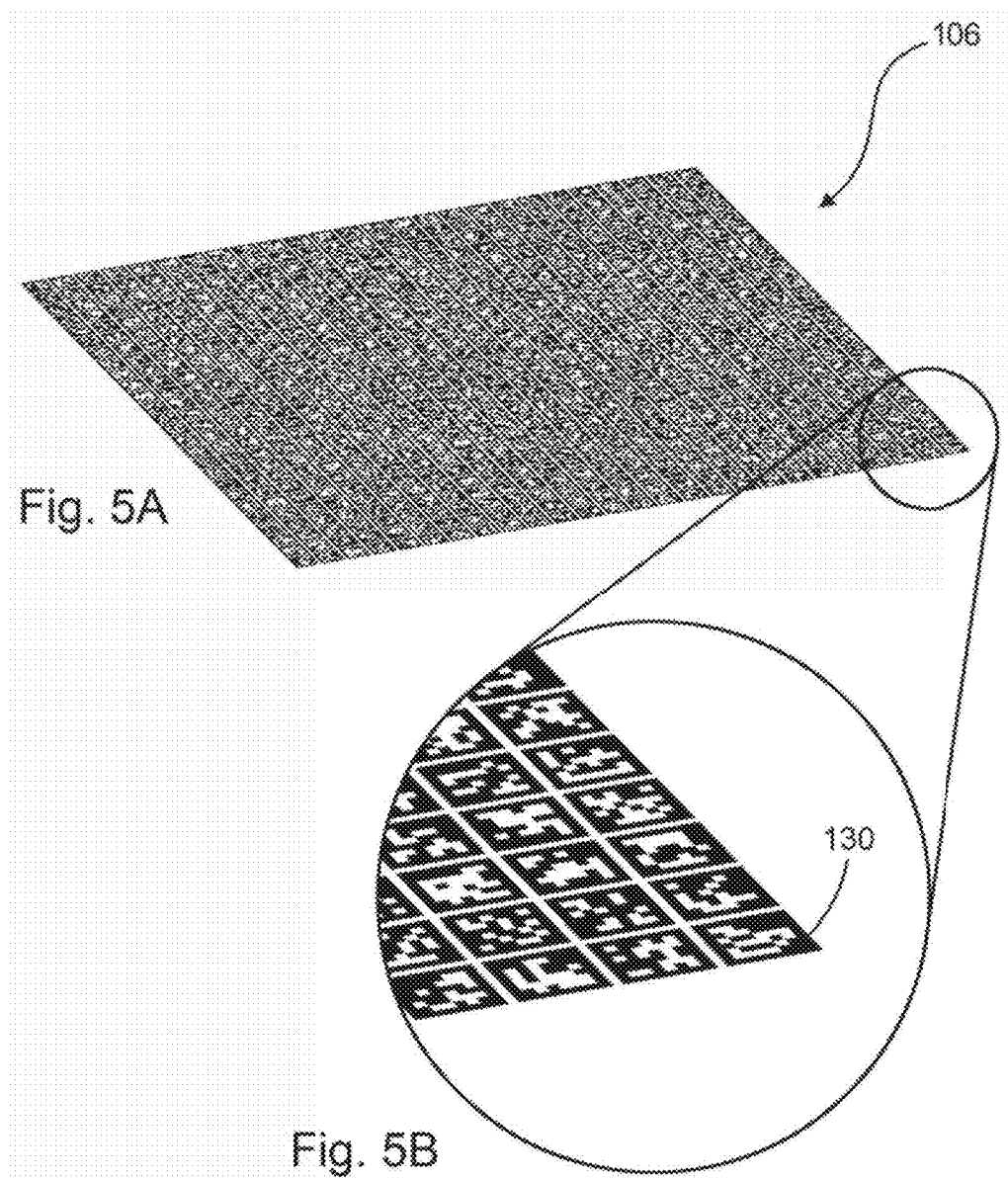

OPTICAL SURFACE TRACKING FOR MEDICAL SIMULATION

CROSS-REFERENCE TO RELATED APPLICATION

This patent application claims the benefit of U.S. Provisional Patent Application Ser. No. 62/798,281, entitled "Marker-Based Inside-Out Optical Tracking for Ultrasound Simulation," filed Jan. 29, 2019, which application is incorporated in its entirety here by this reference.

BACKGROUND

Ultrasound simulation is a vital tool in allowing medical students and professionals to learn the intricate hand-eye coordination and diagnostic skills necessary to perform accurate patient assessment and procedures. Real handheld ultrasound probes allow the user to manipulate the device both translationally (e.g. adjusting the position along the surface of the skin) and rotationally (e.g. adjusting the orientation through rocking and fanning) in order to obtain the optimal view or views to diagnose a patient or perform a procedure. Therefore, a robust ultrasound simulator would ideally offer a full 3D (six degree-of-freedom, or 6-DOF) range of motion. With the level of motion tracking afforded by the proposed invention, the position and orientation of a mock ultrasound probe or syringe with respect to an optical surface can be processed by an ultrasound simulator to compute and display the proper ultrasound image as if a real clinical probe or syringe were placed on a real patient in the same position and orientation.

Currently available ultrasound simulation solutions use either internal motion-sensing technologies (e.g. accelerometers and gyroscopes) that deliver 3-DOF (i.e. orientation as yaw, pitch, and roll) tracking or larger, more complex, and more expensive technologies (e.g. magnetic trackers) that deliver 6-DOF tracking (i.e. position and orientation). Such existing 6-DOF options are not practical for individual users due to logistical (e.g. large form factor) and cost considerations, thereby limiting ultrasound training options. Furthermore, existing optical tracking technologies (i.e. external tracking solutions) that have been paired with ultrasound simulators are limited by "line-of-sight" dependence. Extreme angles and physical obstructions (e.g. a user's hand or finger) often limit the tracking capabilities of these solutions.

Therefore, there is still a need for a mock ultrasound probe or syringe to deliver a full 6-DOF range of movement using a compact form factor that can deliver an affordable individual user training solution without the aforementioned limitations.

SUMMARY OF THE INVENTION

The present invention is a novel solution whereby a handheld instrument such as a mock ultrasound probe or syringe (also referred to as an optical probe or optical syringe) can be tracked with a full 6-DOF range of motion (i.e. position and orientation). The system uses an internal optical camera to track the positions and orientations of optical markers presented on an optical surface. A single marker allows full 3D tracking when visible. A collection of markers provides redundancy and allows robust tracking as individual markers come in and out of view. In the preferred embodiment, the camera resides inside an enclosed cavity within the handheld device. In the preferred embodiment for a mock ultrasound probe, the camera points toward the head of the probe where the transducer element of a real ultrasound probe would be located (the part of the probe that makes contact with the skin). In the preferred embodiment for a mock syringe, the camera points toward the tip of the needle, where it would penetrate the skin. In some embodiments, mirrors or other reflective technologies can be used so that the camera picks up the intended visual field.

When applied to a mock ultrasound probe, the system leverages the fact that such a device by its nature must generally maintain close contact with a surface (e.g. skin) in order to function. Thus, when the mock probe is placed on an optical surface in the manner of scanning, a camera located inside the enclosure pointing toward the probe head will allow constant visibility of some portion of the optical surface.

Similarly, when applied to a mock syringe, the system leverages the fact that such a device by its nature must generally maintain a clear path between the housing of the syringe and the surface (e.g. skin) being penetrated, as this region must be free of obstructions to allow the housing to move towards the surface as the needle of the syringe is inserted. Thus, when the mock syringe is placed on an optical surface in the manner of a procedure, a camera located inside the enclosure pointing toward the tip of the needle will allow constant visibility of some portion of the optical surface.

This inside-out tracking solution minimizes the problem of occlusions often encountered with other types of tracking solutions, where the camera is placed externally with respect to the object being tracked. With a mock device using an external tracking solution, the user must be careful to avoid blocking the camera view of the device with their hands, resulting in an unnatural grip, and a necessary awareness of the underlying technology. The present system aims to minimize these problems. Furthermore, the present system allows for a more compact product, as all sensors are located within the instrument itself.

BRIEF DESCRIPTION OF THE DRAWINGS

FIG. 5A shows an embodiment of a flat surface.

FIG. 5B shows a close-up of the portion indicated in FIG. 5A.

DETAILED DESCRIPTION OF THE INVENTION

Figure 1:
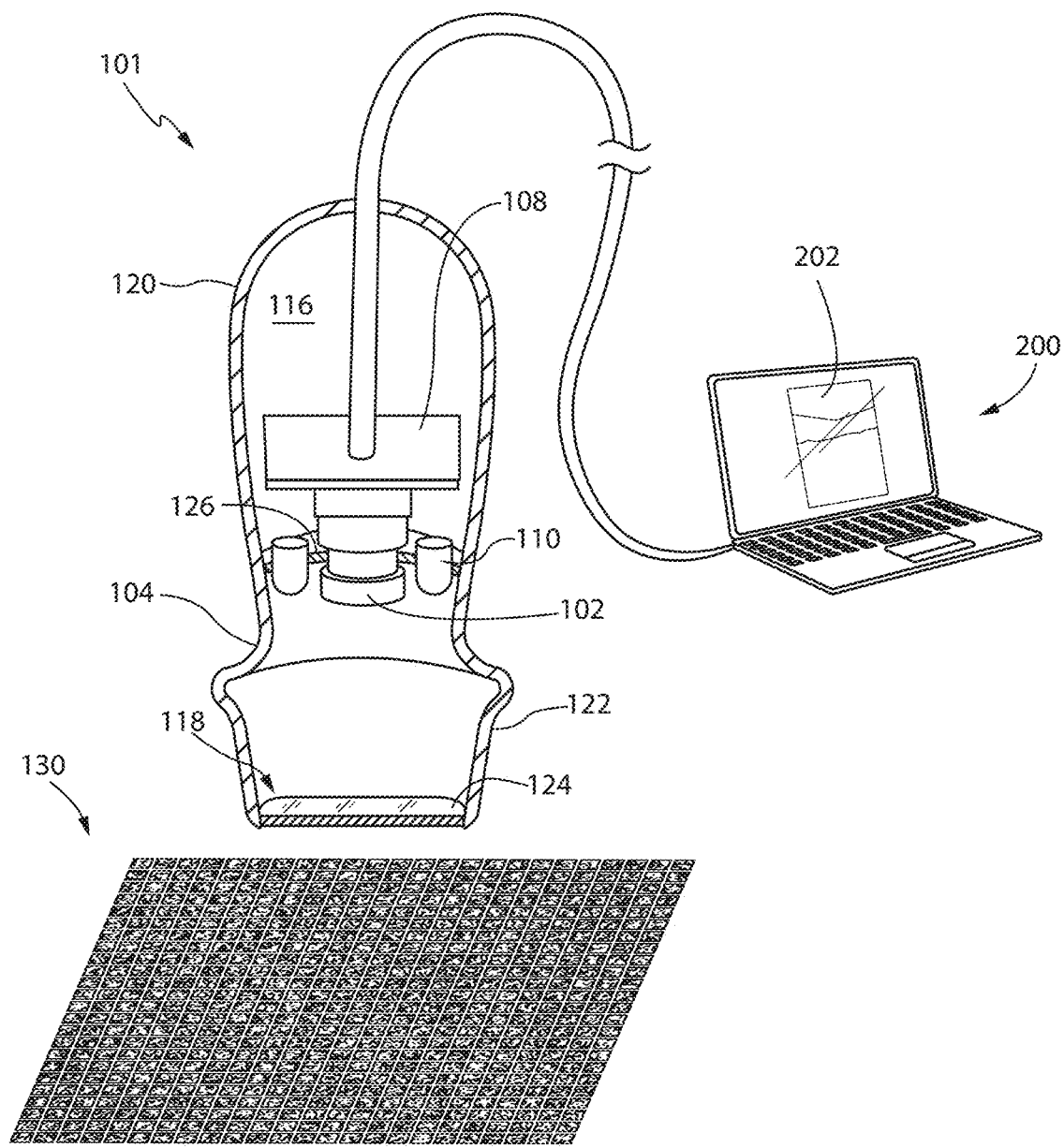
FIG. 1 shows an embodiment of the present system with an instrument shown as a probe, with portions of the enclosure removed to reveal internal components.

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The invention of the present application comprises two main components: an instrument 101 (e.g. a mock ultrasound probe or medical syringe) and a plurality of markers 130. These components are used together to provide tracking information of the instrument 101 to an ultrasound simulator for purposes of training a user how to use a medical instrument, such as an ultrasound probe or syringe.

The Instrument

The instrument 101 is the tool or device that is held by the user and moved about in three-dimensional space through 6-DOF to mimic the use of a medical device. The instrument 101 comprises an enclosure 104, a camera 102, and optionally a light source 110 and a processor 108. Additional electronic components may be included such as ports, heat syncs, and antennas. Furthermore, additional components may be included to mimic the functionality of the medical device being emulated.

In the preferred embodiment, the instrument 101 is used in the medical setting as a teaching and training tool for handling medical devices. The instrument 101 emulates medical devices such as ultrasound probes, syringes, stethoscopes, and the like. As such, the enclosure 104 will have an external appearance that resembles the device being emulated. The camera 102 and other electronic components are housed within the enclosure 104. The enclosure 104 defines an opening 118 through which the camera 102 can view outside of the enclosure 104.

The camera 102 is mounted on the inside of the enclosure 104 in such a way that the camera 102 can obtain a view through the opening 118 of the enclosure 104. For example, the camera 102 can be mounted in the enclosure 104 so as to point toward the opening 118 of the enclosure 104. The opening 118 exposes the internal cavity 116 of the enclosure 104, and can be covered by an optically transparent material 124 (hereinafter "window") that seals and protects the cavity 116 while still allowing the camera 102 to see outside the enclosure 104. If the opening 118 is covered by a window 124, one may choose to keep the window 124 flat or endow it with curvature to minimize possible internal reflections and other undesirable optical artifacts. The window 124 may also be designed to serve as a lens for the camera 102. One may choose a variety of different optically transparent materials for the window 124 to optimize the optical properties of the assembly and minimize visual artifacts. For example, the window 124 may be made of glass, plastic, acrylic, or other appropriate material. The window 124 may also be made up of a combination of different materials, in the form of layers or coatings.

Instrument: Probe Embodiment

With reference to FIG. 1, in the probe embodiment, the instrument 101 is designed to resemble the form of a handheld ultrasound probe. As such, the instrument 101 comprises a handle 120, and a head 122 operatively connected to the handle 120. The head 122 defines the opening 118, which can be covered by the window 124, toward which the camera 102 is pointed, in order to view outside the instrument 101. In some embodiments, the camera 102 can be facing other directions with mirrors 160 directing the view of the camera 102 to the opening 118. The inside of the enclosure 104 is hollow for housing the camera 102 and other electronic components. Preferably, the inside of the enclosure comprises a bracket 126 for rigidly mounting the camera 102 to the enclosure 104. However, the camera 102 can be mounted to the enclosure 104 in a variety of ways, such as friction fit, adhesives, fasteners, clips, magnets, compression fit, snap fit, and the like. Other internal components can be connected the same way.

In some embodiments, a light source 110 may be provided inside the enclosure 104. Preferably, the light source 110 is a light emitting diode, but other light sources can be used. Preferably, the light source 110 is mounted in a manner that allows the light source 110 to illuminate the view of the camera 102. As such, the light source 110 may be mounted adjacent to the camera 102.

Optical Instrument: Syringe Embodiment

With reference to FIGS. 2A-2E, in the syringe embodiment, the enclosure 104 is designed to resemble the form of a syringe, as might be used in a needle guided procedure, wherein a live ultrasound image is used to aid a user in guiding a needle to the target anatomy. As such, the enclosure 104 may be an elongated shaft 148 having a first end 150 and a second end 152 opposite the first end 150. A needle 154 can project out from the enclosure 104 at the first end 150, and a plunger 156 can project out from the enclosure 104 at the second end 152. The first end 150 can define the opening 118, and the camera 102 can be placed inside the enclosure 104 facing the opening 118 so that the optical axis A of the camera 102 is parallel to the shaft 148 of the optical syringe, and pointed towards the needle tip 158. The enclosure 104 takes on a form similar to a clinical syringe, except that the opening 118 will allow the camera 102 to see outside the enclosure 104 toward the needle tip 158.

Figure 2A:
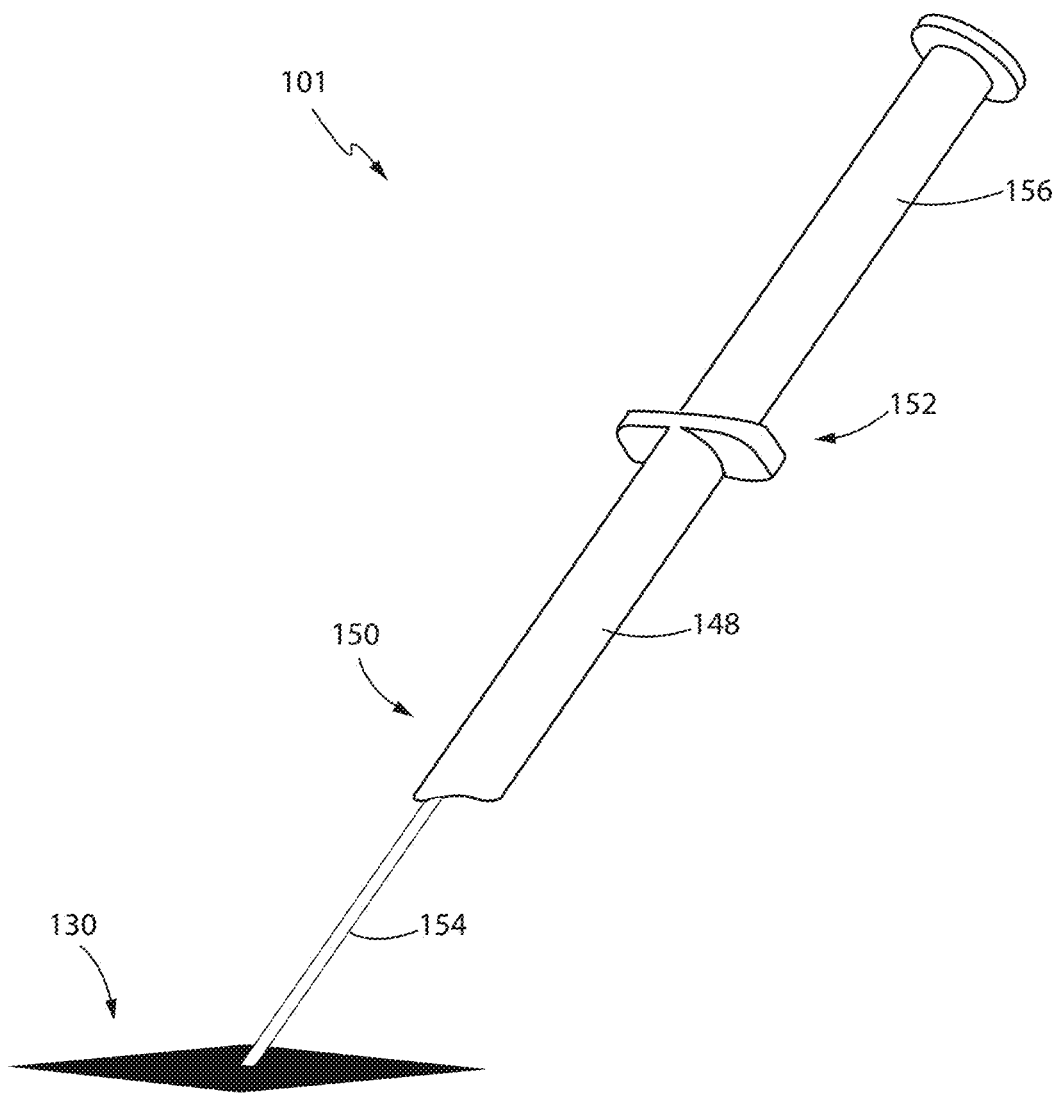
FIG. 2A shows an embodiment of an instrument in the form of a syringe.
Figure 2B:
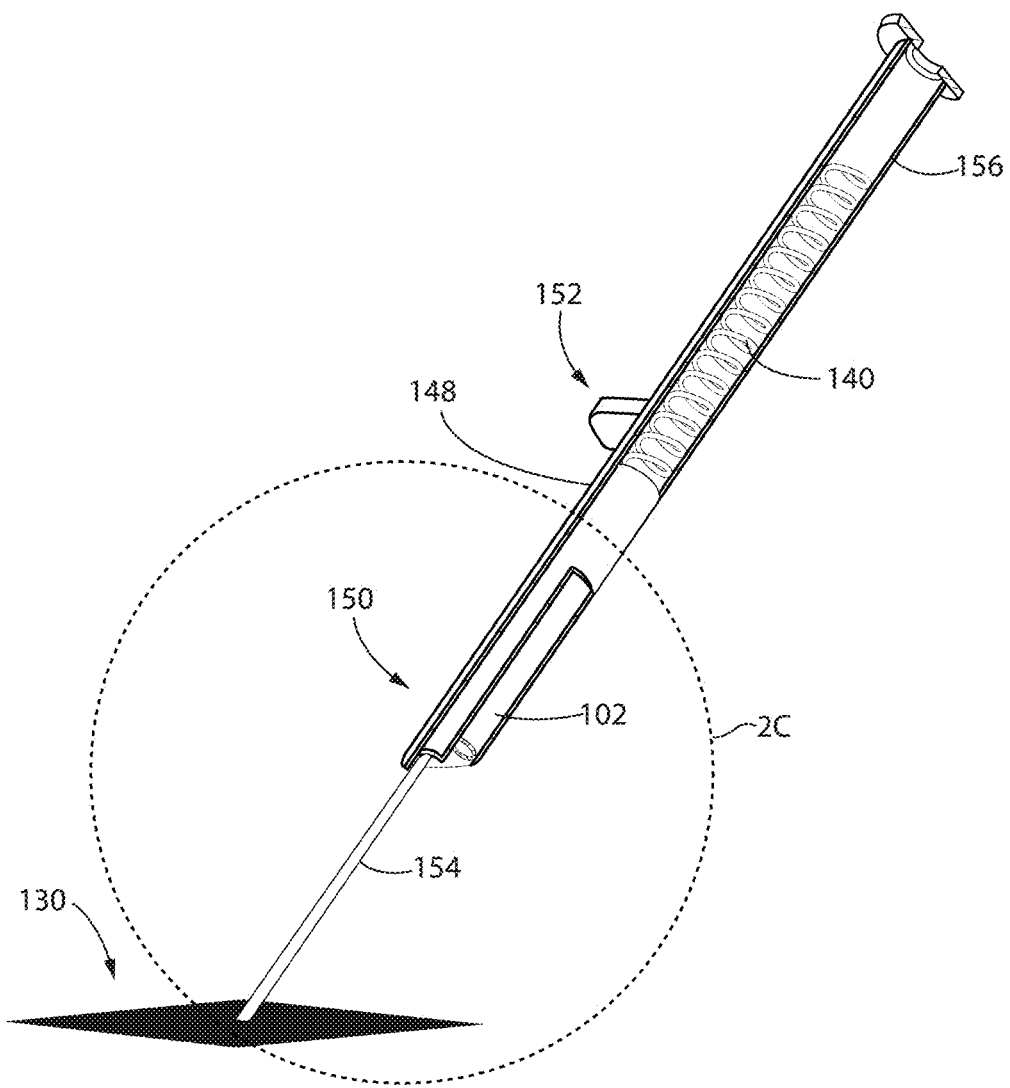
FIG. 2B shows an embodiment of the syringe shown in FIG. 2A, with portions of the enclosure removed to reveal internal components.
Figure 2C:
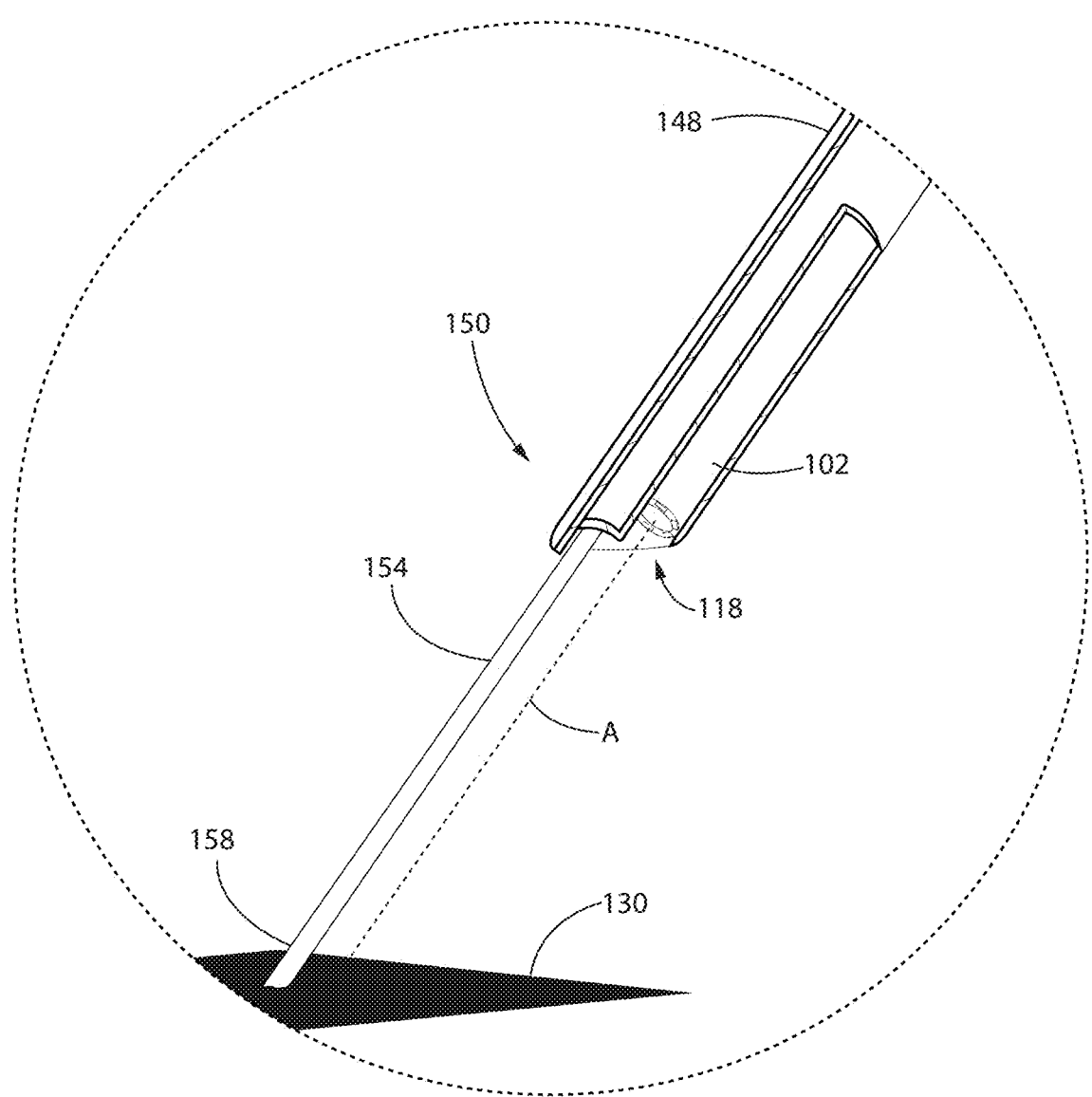
FIG. 2C shows a close up of an embodiment of a portion of the syringe identified as 2C shown in FIG. 2B, with portions of the enclosure removed to reveal internal components.
Figure 2D:
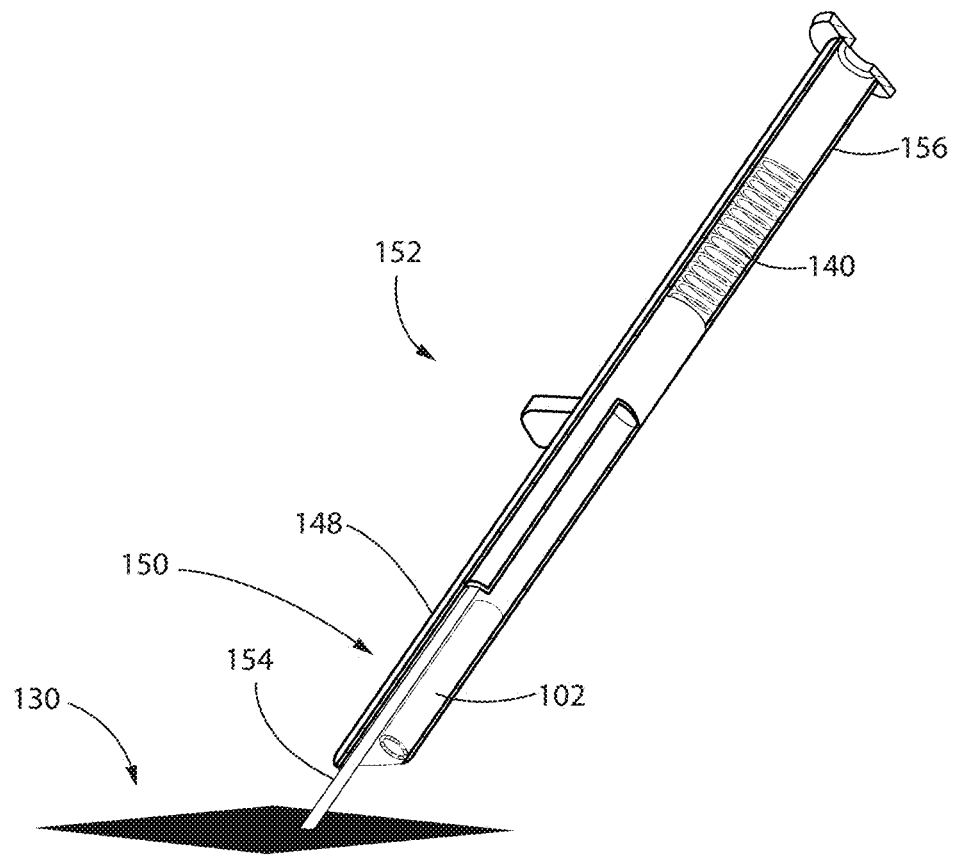
FIG. 2D demonstrates one approach to needle retraction of a syringe embodiment, wherein only the needle retracts into the enclosure.
Figure 2E:
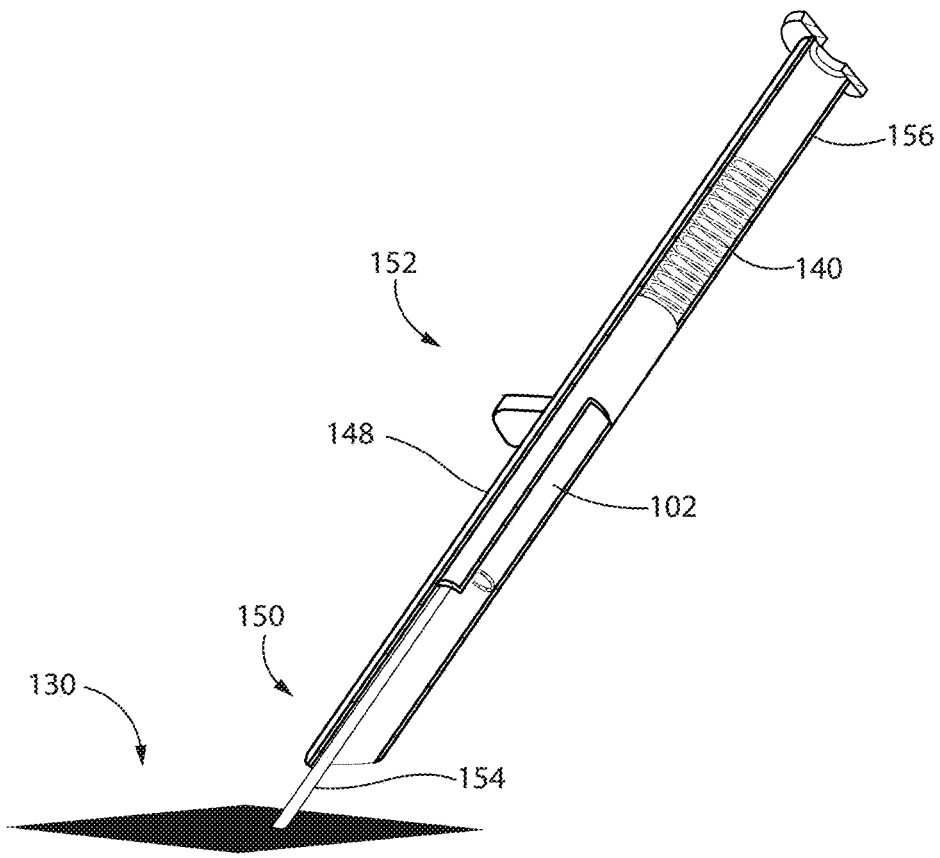
FIG. 2E demonstrates another approach to needle retraction of a syringe embodiment, wherein both the needle and the camera retract into the enclosure, allowing the camera to maintain focus.

The needle 154 may be designed to retract into the enclosure 104 of the optical syringe to allow simulated needle insertions, or it may be fixed, to allow actual needle insertions. If the needle is designed to retract, an elastic device 140, such as a spring, rubber band, or other compressible or stretchable material may be used to provide resistance to retraction and to allow the needle to return to its normal, extended position when force is removed. The camera 102 may be allowed to retract with the needle 154 (FIG. 2E), or stay fixed relative to the enclosure 104 (FIG. 2D). In the case of the camera 102 retracting with the needle, markers 130 or other indicators (such as a measuring line, score lines, numbers, etc.) may be applied within the enclosure 104 to allow the system to determine the amount of retraction.

Optical Instrument: Camera

The camera 102 may be comprised of the standard components of a camera, such as an image sensor, lens assembly, and the required electronics to gather the photographic impressions on the image sensor and transmit them to the processor 108. The camera 102 may either be a component within the enclosure 104, or coupled with the enclosure 104 itself such that the standard components of the camera 102 are placed within the enclosure 104 making the whole assembly function as the camera 102. Mirrors 160 may be employed between the lens assembly and the image sensor to control the flow of light within the enclosure 104, either to better accommodate the form factor of the enclosure 104, or to support multiple views outside the enclosure. The setup may employ multiple mirrors 160 directed at multiple lenses to achieve multiple views outside the enclosure. Waveguides, such as fiber optics, may also be used in this regard.

The placement of the camera 102 or camera components within the enclosure 104 should be chosen in such a way as to afford an optimal view of the optical surface 106 when the device is in use. In the preferred embodiment, the instrument 101 is expected to perform when in close contact with a surface 106. The preferred embodiment employs a fixed focus lens assembly optimized for the range of distances at which the surface 106 must be tracked reliably. In the preferred embodiment of the syringe, a fixed focus lens assembly is used that is optimized for the range of distances at which the optical surface 106 must be tracked reliably, even as the body of the syringe moves closer and farther away from the surface 106 during a simulated procedure. However, an adjustable focus mechanism may also be used here, particularly if the syringe is not designed to allow the camera 102 to slide relative to the enclosure 104 to maintain a fixed distance from the insertion point. Such an adjustable focus mechanism may be controlled via standard focusing techniques, or by the needle insertion distance, either mechanically or through software.

An image sensor should be chosen to allow adequate resolution and frame rates for the desired application. While a global shutter is preferred for robust tracking, a rolling shutter may also be used if the shutter speed is adequate relative to the expected speed of movement of the instrument. In the preferred embodiment, the image sensor may be capable of detecting light in the infrared spectrum.

Various camera parameters well known to those skilled in the art may be known to the processor 108 to facilitate accurate position and orientation estimation and to eliminate lens distortions to provide high quality tracking. A one-time calibration procedure may be performed to determine these parameters.

Optical Instrument: Light Source

Since the enclosure 104 blocks out most external light, the instrument 101 may provide its own source of illumination to make the surfaces 106 visible to the camera 102. In the preferred embodiment, the light source 110 is located inside the enclosure 104 and points toward the viewing window 124 to illuminate the optical surface 106. However, the light source 110 may also be located outside of the enclosure 104 or on or behind the optical surface 106 as backlighting. One skilled in the art understands that the wavelength of the light source 110 must match the spectrum of light that the optical camera 102 is capable of sensing.

In the preferred embodiment, the light source 110 emits light in the infrared spectrum, which is invisible to the human eye. This is done to minimize distractions that would otherwise result from visible light being emitted from the instrument 101. Furthermore, since most indoor light sources do not emit light in the infrared spectrum, operating in the infrared spectrum minimizes optical interference from outside light sources, which are expected to be present in typical settings where this invention may be used. Operating within the infrared spectrum also allows the surface 106 to conceal the markers 130 from the human eye.

Optical Instrument: Processor

The camera 102 transmits image data to a processor 108 hosting an algorithm that computes the position and orientation of the instrument 101 with respect to the surface 106. The camera 102 and the processor 108 may be connected physically using a wire, or wirelessly using a protocol such as USB, Thunderbolt, Bluetooth, Wi-Fi, or a custom protocol. The processor 108 may be a microcontroller placed inside the enclosure 104, a remote device placed outside the enclosure 104, or a component of a more complex computing system 200 that is separate from the main instrument 101 discussed in this invention.

Optical Surface

With reference to FIGS. 5A-9, in our invention, an optical surface 106 refers to any surface displaying one or more markers 130, generally in close proximity to one another. This surface may take on several forms: a flat surface, a curved surface, or a combination thereof. Surfaces that are curved can mimic various anatomical structures, such as organs and bodily cavities. As such, on curved surfaces, the markers can be placed on the external surface or the internal surface.

Optical Surface: Flat

In the flat surface embodiment as shown in FIGS. 5A-5B, the surface 106 can be either a rigid or semi-rigid flat surface, or a flexible surface that can be made flat or conform to the shape of another object. In its flexible form, the surface 106 may be used to conform to other surfaces, particularly when used as a sticker or other attachable surface 106 applied to a human, animal, medical manikin, laptop, or other desirable surface. In one of the preferred embodiments of the surface 106, the surface 106 is a flexible sticker (also called an optical tag) that encodes a specific body region (e.g. clavicle) intended to be placed on a human or manikin in the position and orientation corresponding to the encoded region. By way of example only, the optical tag may be approximately 7 cm by 7 cm. Several of these optical tags can be placed on the human or manikin at the same time, allowing the user to scan different regions of the body by scanning different optical tags.

In another preferred embodiment of the surface 106, the surface 106 is flat and rigid, and is intended to be used on a desk or other surface to scan without a human or manikin.

Optical Surface: Three-Dimensional Models

In some embodiments, the surface 106 can be a three-dimensional model. For example, the surface 106 can be a three-dimensional geometric shape (see, FIGS. 6A-6B, 8A-8B, and 9), or the surface 106 can be a three-dimensional model of a human body or human body parts (see, FIGS. 7A-7B). So as to be able to stand on its own, the three-dimensional model can be a rigid or semi-rigid structure. In addition, the three-dimensional model can be comprised of surfaces 106 that are flat, curved, or a combination of flat and curved surfaces. Furthermore, the three-dimensional model can be solid having visible exterior surfaces 180, or hollow having visible exterior walls 180 as well as interior walls 182 defining a cavity 184. In solid three-dimensional models, the markers 130 are attached to the visible exterior surfaces 180. In hollow three-dimensional models, the markers 130 can be attached to the exterior surfaces 180 or the interior surfaces 182.

For example, the surface 106 can be a rigid or semi-rigid curved or faceted surface 106, generally resembling or mimicking an exterior anatomical region of a human or animal, or even an entire body. The surface 106 may be open or closed, and may enclose a solid or hollow volume. The markers 130 can be displayed on the outside of the surface representing the skin. Examples of such an embodiment are a head, an arm, or a more generic curved surface that may be used as a stand in for multiple types of anatomy.

In another example, the surface 106 can be a rigid or semi-rigid curved or faceted surface 106, generally resembling an interior anatomical region of a human or animal, such as a body cavity. This embodiment can take on at least two distinct forms: First, the surface 106 may resemble a narrow tube (straight or curved) (see, FIG. 8A) where a mock endoluminal ultrasound probe would maintain close contact with one of the sides of the surface 106 at all times. This is useful for simulating, for example, esophageal or endorectal scanning. Second, the surface 106 may resemble a larger cavity (see, FIG. 9) where a mock ultrasound probe may not always maintain close proximity to one of the sides. In this embodiment, the markers 130 may be larger than in other embodiments, as the markers must be visible across a larger range of distances. This is useful for simulating, for example, endovaginal scanning.

In some embodiments, the surface 106 may be designed to accommodate any combination of the specific surface 106 types. For example, the surface 106 can be a complete manikin that includes both an external skin and interior pathways, or simply a head that also contains a throat (see, FIG. 7A). A plurality of markers 130 can be attached to the external and internal surfaces of the manikin. In some embodiments, a more generic scannable surface 106 not meant to represent a specific anatomical region may contain flat regions as well as exterior and internal curved surfaces. Markers 130 can be attached to the flat regions, curved regions, internal surfaces, and external surfaces.

Markers

A marker 130 is a 2D visual pattern that has a distinct appearance. In some embodiments, each marker 130 encodes a unique numerical value. Importantly, a marker 130 provides adequate shape information from which to estimate any 3D transformation (i.e. translation and rotation, or position and orientation) relative to the camera 102. Preferably, the markers 130 should be chosen such that they can be:

Robustly distinguished from background noise in a scene or from other confounding factors, such as glare or internal reflections.

Encoded with a numerical value that can be robustly recovered from observations at a broad range of angles.

Designed with adequate shape information such that projection transformations (which include position and orientation information) can be robustly recovered from observations at a broad range of angles.

Figure 4A:
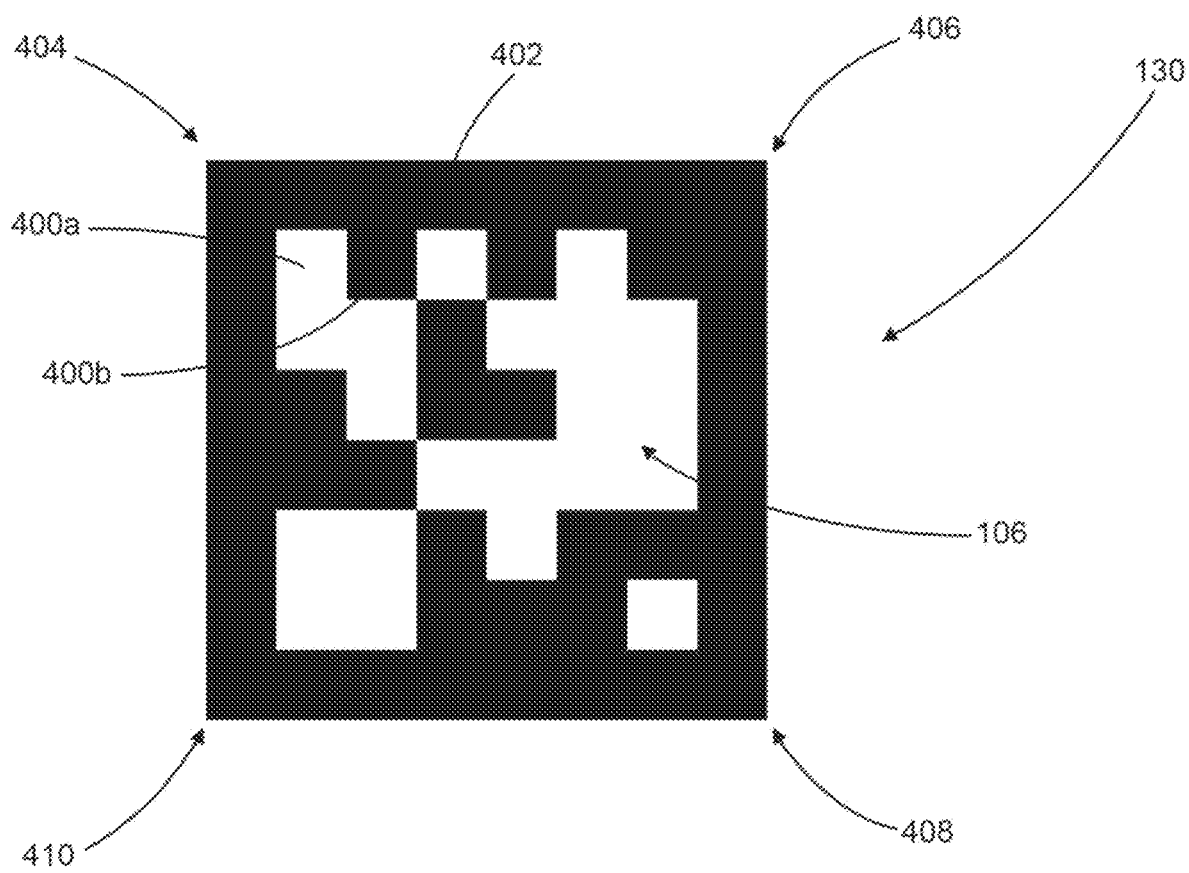
FIG. 4A shows an embodiment of a marker.

In the preferred embodiment, ArUco markers 130 can be used. For example, with reference to FIG. 4A, the marker 130 can comprises an n×n grid of small squares 400a, 400b surrounded by a border 402. In the example in FIG. 4, the grid is a 6 by 6 grid surrounded by a black border 402. Each of the n×n squares 400a, 400b can be one of at least two contrasting colors. In the example in FIG. 4, each n×n square 400a, 400b is either black or white; however, additional colors can be used to increase the number of distinct markers. The contrast of black and white squares improves the processor's ability to recognize and interpret the marker 130. The border 402 of the grid should contrast with the background so that one marker can be distinguishable from another marker. In the example in FIG. 4, since the background is white, the border is shown as black. The remainder of the squares 400a, 400b within the border 402 can be black or white. These small squares 400a, 400b will be referred to more generically as pixels 400a, 400b, as these are the smallest, fundamental unit that make up the marker 130, and the shape of the pixels 400a, 400b need not be squares. For example, the pixels 400a, 400b can be circular, triangular, rectangular, and the like.

The arrangement of the contrasting squares is unique for each marker allowing the marker 130 to encode a variety of information through the arrangement of these squares. For example, the marker 130 can encode anatomical information, position and orientation information, a unique numerical value, and the like, based on the arrangement of the squares. The arrangement of squares is specially designed to avoid rotational symmetries, so that the encoded numerical values can be decoded unambiguously from any viewpoint. In other words, rotating a marker 90, 180, 270 degrees, or any angle between zero and 360 degrees, will still result in a unique pattern that no other marker 130 will match. This is mandatory when the viewing angle is arbitrary. Similarly, the markers 130 can also be designed to be reflection invariant (i.e. flip invariant), which may be useful if displayed on a transparent surface that could be viewed from either side. The preferred embodiments of the optical probe 112 and syringe use optical surfaces 106 with n=6 for a 6×6 grid of squares within the border of each marker 130.

Optical Surface: Marker Placement

The size, shape, and spacing of the markers 130 on the optical surface 106 can be arbitrary, but must be known to the processor 108 in advance. The preferred size, shape, and spacing of the markers 130 depend on the application, and may vary from marker 130 to marker 130 within a given surface 106 (i.e. per-marker 130 size, shape, and spacing parameters). The size of a given marker 130 should be chosen to maximize the number of markers 130 visible through the window 124 of the enclosure 104 while remaining large enough that the optical camera 102 can robustly resolve the details of each marker 130, including any encoded information, such as a numerical value and its corners, used for position estimation. For example, the relative positions of the four corners 404, 406, 408, 410 of a square can provide information regarding the angle of view of the square. If the four corners 404, 406, 408, 410 of a square are equally spaced apart from each other, the view is perpendicular to the square. If however, the relative positions of the corners 404, 406, 408, 410 are skewed (i.e. not equidistant from each other as should be expected in a square), then the angle of view is not perpendicular and/or directly above the marker 130.

These parameters should be optimized with consideration for all optical tracking instruments intended to be used with the given surface 106. By way of example only, for surfaces 106 intended to be used with the ultrasound probe and syringe embodiments, each marker 130 can be a square having dimensions of around 4 mm per side. Smaller dimensions can be used so long as the resolution of the marker 130 is clear enough for the camera to and distinguish from other markers 130.

In some embodiments, the unique numerical value of each marker 130 corresponds to its physical position and orientation on the surface, allowing a tracking algorithm to know exactly where the optical probe 112 is with respect to the surface 106. The processor 108 must know these positions and orientations in advance, either through an algorithmic mapping or a look-up table:

Algorithmic Mapping. The position and orientation of each marker 130 may be determined by an algorithm, such as when markers 130 are arranged in a simple 2D grid pattern. In such a case, applying integer division and the modulus function can allow an algorithm to compute a marker's position given its encoded numerical value. Algorithmic mappings can either be computed on the fly, or precomputed and stored in a look-up table.

Look-Up Table. The position and orientation of each marker 130 may be determined by a look-up table, mapping a numerical value to a 3D position and orientation. This is desirable when the positions and orientations of markers 130 are not defined by a simple algorithm, such as when markers are placed manually on a surface. If the marker 130 positions and orientations are set virtually (e.g. placed on a virtual model), the look-up table can be computed directly from this information, and then the virtual model constructed in the physical world, by means described later. If, however, the marker 130 positions and orientations are set in the physical world (e.g. stickers placed on a physical surface), then the look-up table must be computed by first determining the physical position and orientation of each marker 130, as described below.

One may create a set of surfaces 106, each bearing a distinct collection of markers 130. If care is taken to ensure that the numerical value of each marker 130 is unique not only within a single surface 106, but also across the entire set of optical surfaces 106, the processor 108 may use this information to uniquely identify which surface 106 in the set is being observed, given the observations of a single marker 130. This many-to-one mapping can be achieved either through an algorithmic mapping or a look-up table, similar to the methods described for determining a marker's position and orientation. Thus, in addition to each marker 130 encoding a unique numerical value, each surface 106 may also encode information, such as a unique numerical value or anatomical region of interest, allowing the processor 108 to know which optical surface 106 is being observed.

One may use the numerical value of an optical surface 106 to assign it a specific anatomical region of interest. Subsequently, when the user manipulates the probe 112 or syringe over a specific optical surface 106, the processor 108 will not only compute the position and orientation of the optical probe 112 or syringe with respect to the optical surface 106, but it will also determine which anatomical region is being scanned. The processor 108 can then use this information to compute and display the appropriate ultrasound images for that anatomical region. When the user switches to scanning a different optical surface 106, the processor 108 will automatically compute and display images for the new region based on the unique arrangement of markers in that region.

Optical Surface: Construction Techniques

Figure 4B:
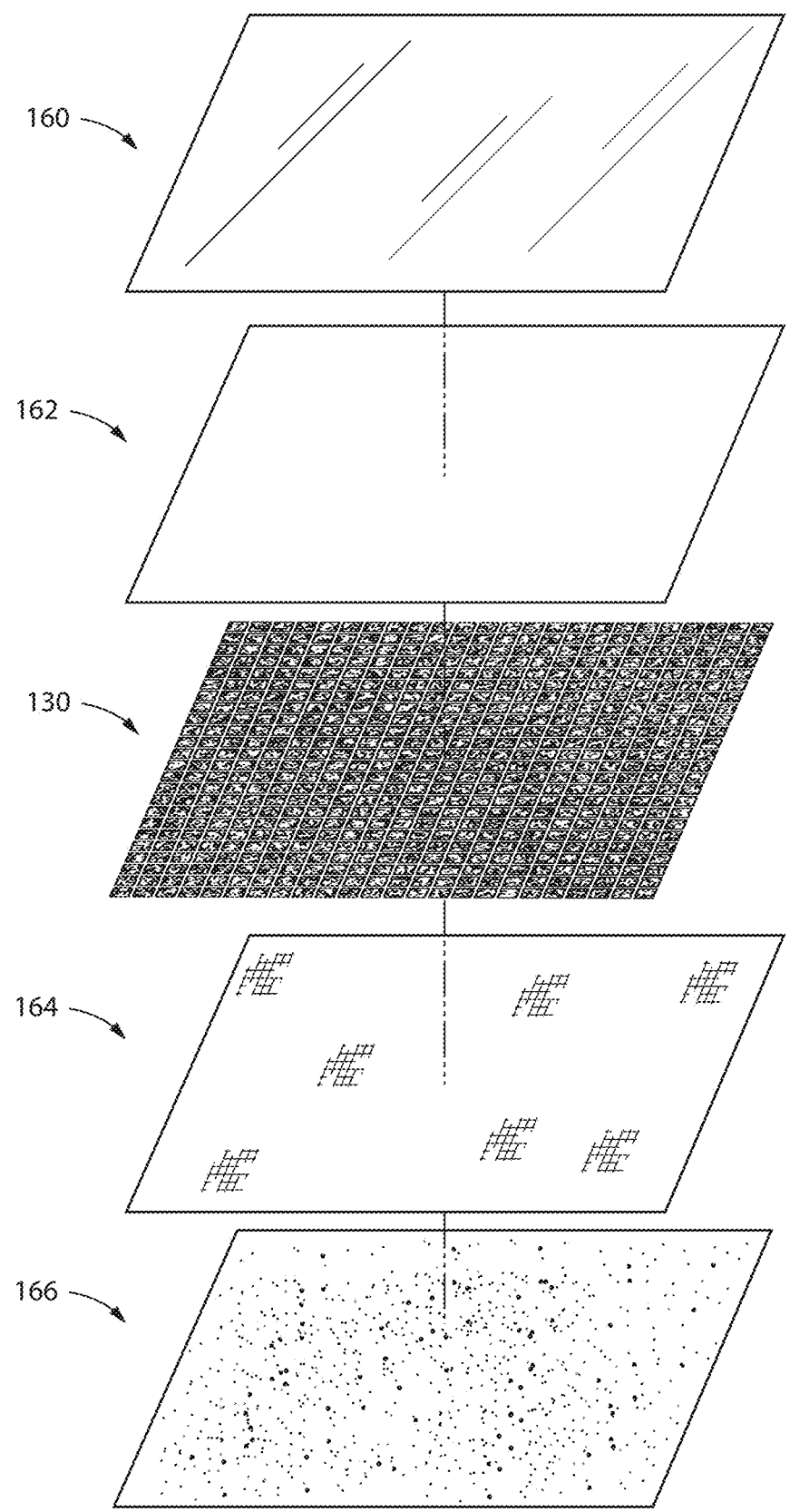
FIG. 4B shows a layered optical tag.
Figures 6A, 6B:
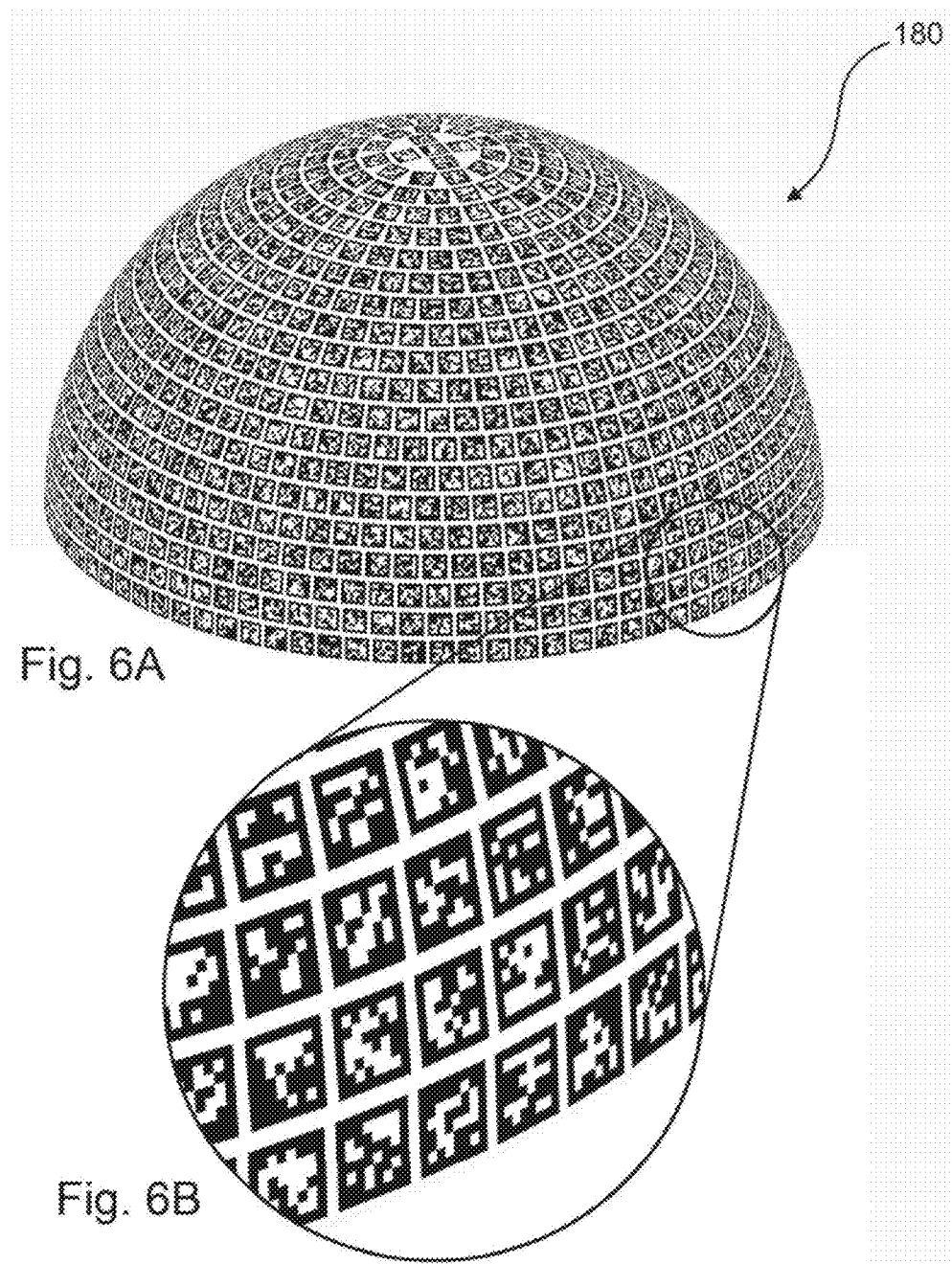
FIG. 6A shows an embodiment of a curved external surface.
FIG. 6B shows a close-up of the portion indicated in FIG. 6A.
Figures 7A, 7B:
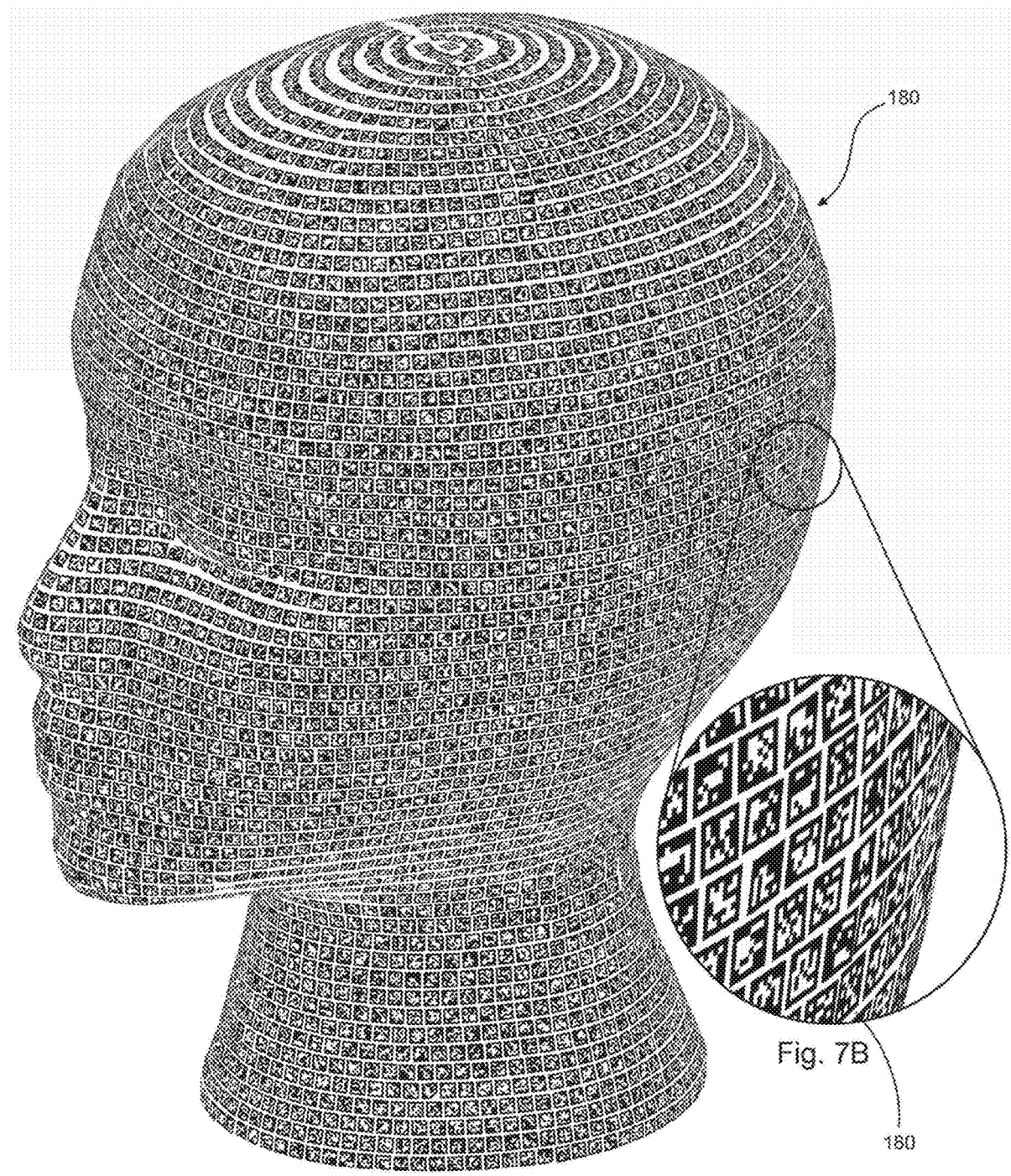
FIG. 7A shows an embodiment of a more complex curved external surface.
FIG. 7B shows a close-up of the portion indicated in FIG. 7A.
Figures 8A, 8B:
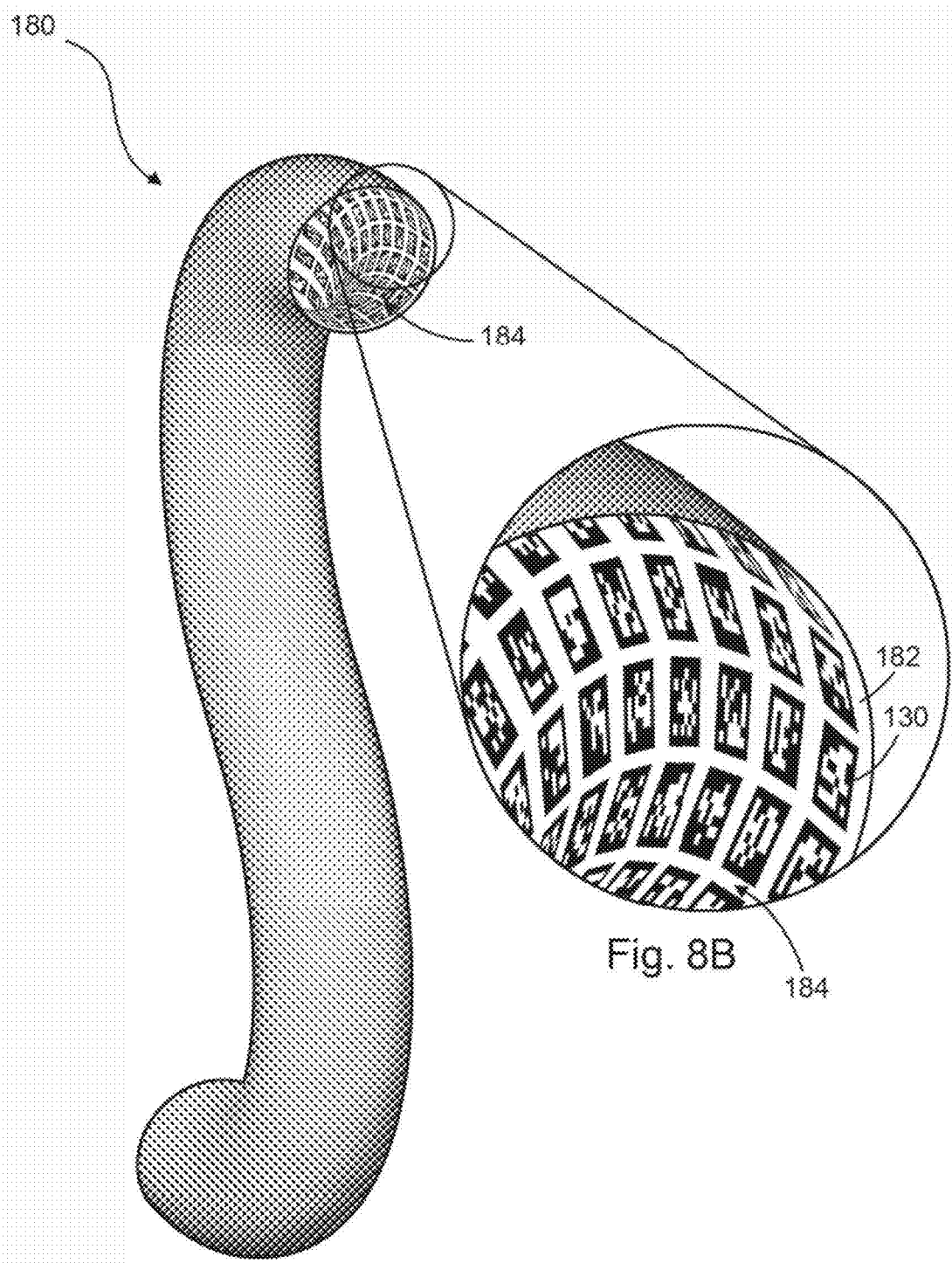
FIG. 8A shows an embodiment of an internal surface.
FIG. 8B shows a close-up of the portion indicated in FIG. 8A.
Figure 9:
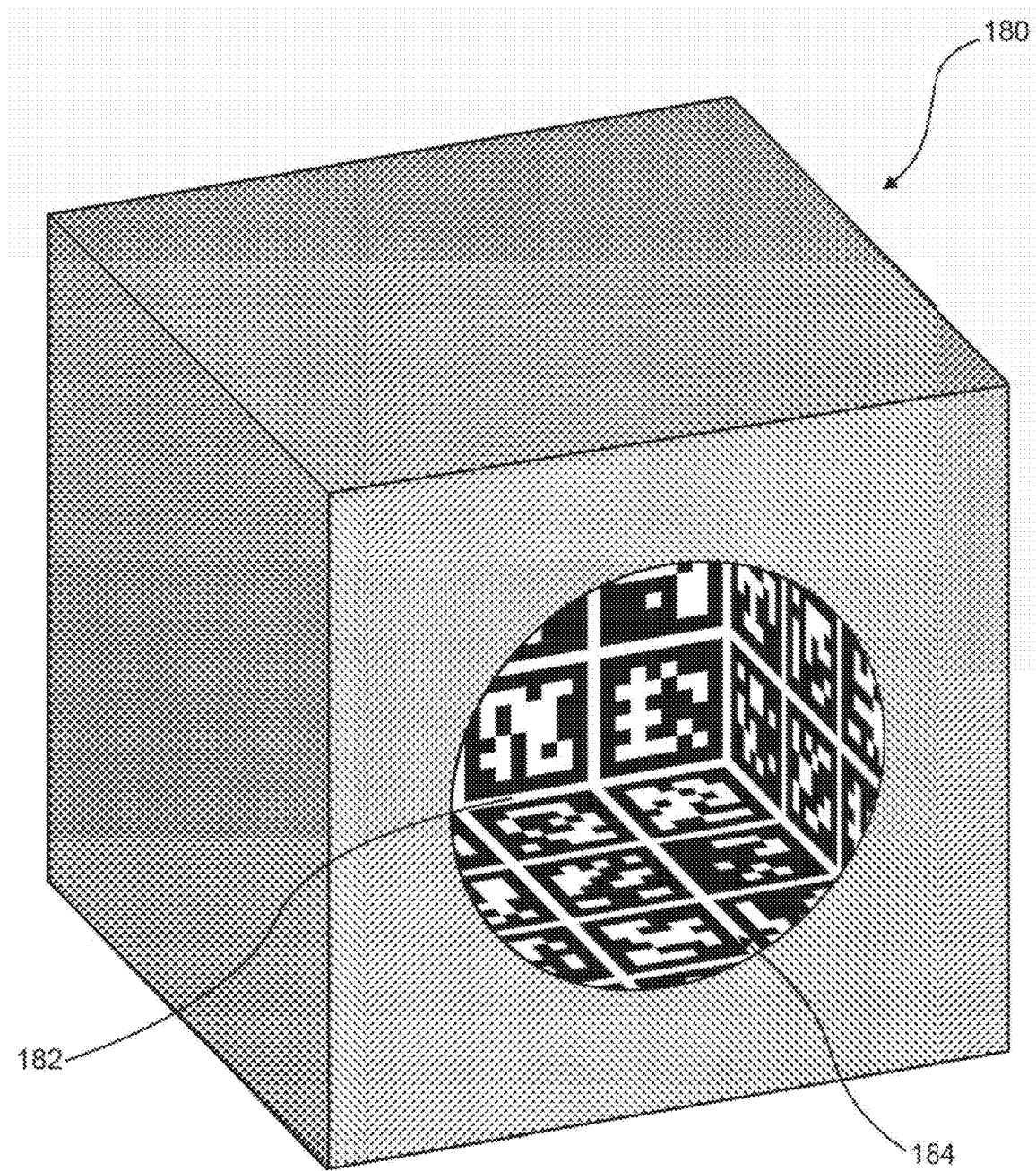
FIG. 9 shows an embodiment of another internal surface with large markers to allow tracking even when a probe loses contact with the surface.

The methods of producing these surfaces 106 varies depending on the type of surface. A flat surface (i.e. an optical tag) may be printed on standard paper with standard inkjet or laser printing technologies. In the preferred embodiment, as shown in FIG. 4B, multiple layers (enumerated below from bottom to top) are combined with the display layer to imbue the optical tag with additional properties:

An adhesive layer 166 for attaching to a human, manikin, or other surface.
A semi-rigid layer 164 for strength.
A display layer bearing the grid of markers 130 (printed, electronic, or other)
An aesthetic layer 162 for color, patterns, or text.
A transparent, minimally reflective layer 160 for protection and anti-glare properties.

Additional layers may be added to further alter the properties of the tag 106, such as a foam layer to add thickness and improve its ability to conform to various surfaces.

In some embodiments, the markers 130 may be displayed on an electronic screen, such as those found on smartphones, tablets, and laptops. The markers 130 may also be displayed on digital paper, such as the commercially available products provided by E Ink. In another embodiment, the markers 130 may be applied directly existing surface (e.g. a user's skin) through means of an ink stamp, temporary tattoo, and the like.

Curved surfaces 106 may require more complicated means of production. These generally fall into two categories: Surfaces 106 with their marker 130 positions and orientations defined virtually, and then constructed physically; and surfaces 106 with their marker 130 positions and orientations defined physically, and then constructed virtually (see FIG. 7A).

Curved surfaces 106 with their marker 130 positions and orientations defined virtually may have these positions and orientations set by various means, either algorithmically or manually. Algorithmic means may involve simple mathematical patterns such as grids or spirals, or more complex patterns involving sophisticated algorithms for evenly spacing markers 130 on a surface. Such algorithms may borrow concepts from mathematics, statistics, physics, biology, texture generation, and more. These algorithms may or may not involve a certain degree of pseudo-random number generation. Alternatively, marker 130 positions and orientations may be defined virtually by manual means, such as through interactive software involving a mouse and keyboard, or through an augmented reality or virtual reality setup.

Once a surface 106 and its marker 130 positions and orientations are defined virtually, the surface 106 may be constructed in the physical world through various means:

- Multimaterial, dual-tone, or color 3D printing. The most straight-forward means of constructing an optical surface 106 in the physical world is through 3D printing techniques that include color information.
- 3D printing with relief. Non-color 3D printing techniques can be used to construct the optical surface 106 in the physical world by replacing color information with insets (e.g. grooves) in the model. Once printed, the resulting insets can then be filled with paint or other material to reintroduce color information into the surface 106. Conversely, the raised portions can be painted to reintroduce color information onto the surface 106. Additionally, both the insets and raised portions can be painted. Alternatively, if designed properly, the physical surface 106 can be used as is with backlighting, in the form of a lithophane, wherein thinner regions allow more light through, resulting in a brighter appearance in those areas, allowing the markers 130 to be visible.
- Subtractive Computer Numerical Control. Rather than 3D printing an optical surface 106 with color replaced by insets, standard subtractive computer numerical control machines can be used to carve the surface 106. The same techniques as described previously can then be used on the resulting physical surface 106 to produce the desired color or contrast patterns of the markers 130.
- Laser marking, etching, and engraving. A base optical surface 106 without markers 130 can be constructed through means such as 3D printing or computer numerical control, and then the marker 130 patterns can be added through laser marking, laser etching, or laser engraving.
- Robotic drawing, stamping, and stickering. A base optical surface 106 without markers 130 can be constructed through means such as 3D printing or computer numerical control, and then the marker 130 patterns can be added by a robotic mechanism capable of applying ink through means of a pen, stamp, or other ink applicator. Alternatively, the robotic mechanism may apply stickers bearing the appropriate markers 130 printed by other means.
- Folding. Certain types of optical surface 106 topologies may be constructed as flat surfaces that can then be folded or otherwise bent or stretched to conform to the desired surface 106 shape, either on its own or on top of an underlying structure.
- Photography. A base optical surface 106 without markers 130 can be constructed through means such as 3D printing or computer numerical control, and then the marker 130 patterns can be added by photographic means such as cyanotype techniques. This may use projectors or lasers to expose the appropriate areas, or silhouette shapes to shadow areas that are not to be exposed.
- Vacuum Forming. Flat sheets of markers 130 may be printed or otherwise constructed, and then formed to the desired shape of the optical surface 106 through means of vacuum forming.
- Hydro Dipping. A base optical surface 106 without markers 130 can be constructed through means such as 3D printing or computer numerical control, and then the marker 130 patterns can be added by hydro dipping.

Curved surfaces 106 with their marker 130 positions and orientations defined physically may have these placements set by various means:

- Stickers. Markers 130 can be printed on 2D sticker sheets and then applied by hand to the base optical surface 106.
- Ink stamp. An ink stamp or set of ink stamps can be designed to transfer a marker 130 or set of markers 130, and then used by hand to apply the markers 130 to the base surface 106.
- Other techniques. Any of the techniques described for constructing virtually-defined optical surfaces 106 in the physical world may involve a certain amount of manual involvement or mechanical variance that make the results inconsistent or unpredictable, resulting in new positions and orientations that have now been defined physically rather than virtually. Virtually placed markers 130 may also be augmented with physically placed markers 130 (see FIG. 7B).

Once a surface 106 and its marker 130 positions and orientations are defined physically, the surface 106 may be constructed in the virtual world through various means:

- Photogrammetry. This process involves taking several (potentially hundreds) high-quality photographs of the optical surface 106 from different positions and orientations and then applying algorithms well known to those skilled in the art to generate an accurate 3D virtual model of the surface 106 complete with color information. Computer vision algorithms similar to or the same as those used during the optical tracking process can then be used to detect the markers 130 on the virtual model to determine their precise position and orientation.
- Robotic scanning. This process involves mounting a camera to a robotic mechanism that can view the optical surface 106 from various angles. Computer vision algorithms similar or the same as those used during the optical tracking process can then be used to detect the markers 130. Using knowledge of the robotic arm configuration at the time of each photo, as well as information about the detected markers 130 within the photo, the system can determine the precise position and orientation of each marker 130.
- Tracked scanning. Similar to robotic scanning, any well tracked camera system can be used to identify the precise position and orientation of each marker 130.

Optical Surface: Materials

A surface 106 may be constructed out of any number of materials or combination of materials depending on the construction method used. Materials may include plastics, papers, metals, rubbers, fabrics, glass, wood, pigments, and the like, or any combination thereof. The materials should be chosen to offer the desired level of flexibility or rigidity. In the optical tag embodiment, the materials may be highly flexible to conform to other surfaces. In the curved embodiments, the materials may be more rigid to maintain their form. If used in conjunction with a needle intended to penetrate the surface 106, the surface 106 should be made of materials resilient to multiple penetrations. An example of this might be a metal mesh surrounded by a layer of rubber.

Some embodiments of the surface 106 may provide a fastening mechanism to affix it onto a subject, such as a person, animal, manikin, desk, wall, or even another optical surface 106. For example, the fastening mechanism may be an adhesive backing, or it may comprise pins, screws, hook-and-loop fasteners, magnets, hooks, buttons, rails, and the like.

Optical Surface: Appearance

A surface 106 may be designed in such a way as to hide the markers 130 from being visible to the user. This is desirable to create a more realistic simulation experience, and to avoid visually distracting the user. Hiding the markers 130 can be achieved through operating outside the visible wavelength of light, for example infrared or ultraviolet. In the preferred embodiment, we operate in the infrared spectrum, since many low-cost consumer-grade image sensors are capable of detecting light at this wavelength, and infrared is generally safer than ultraviolet. There are several ways in which the infrared (or ultraviolet) wavelength can be leveraged to obscure the markers 130 from the user:

Covering the markers. By placing a visibly opaque but infrared transparent layer over a visible spectrum display of markers 130, the visibility of the markers 130 can be reduced or eliminated. Alternatively, for a backlit embodiment of an optical surface 106, a layer that is mostly opaque in both the visible and infrared spectrums could cover and hide the markers when the backlight is turned off, but allow the markers 130 to be visible when the backlight is turned on. If an infrared backlight is used, the markers 130 will remain hidden in the visible spectrum.

Using colors that show up lighter in infrared. By displaying the markers 130 in colors that show up lighter in the infrared spectrum than the visible spectrum, and matching the background color in the visible spectrum, the markers 130 can be made to appear only when viewed in the infrared spectrum.

Using colors that show up darker in infrared. By displaying the markers 130 in colors that show up darker in the infrared spectrum than the visible spectrum, and matching the background color in the visible spectrum, the markers 130 can be made to appear only when viewed in the infrared spectrum.

A combination of techniques. A combination of the above techniques may be used.

In addition to wavelength-dependent techniques for hiding the markers 130, other techniques may be used, such as using marker features that are small enough so as to be less apparent to the user, or visible patterns that obscure or camouflage the markers 130. These techniques may also be combined with wavelength-dependent techniques.

To aid the user in distinguishing one optical surface 106 from another and in placing them in the correct anatomical position and orientation (particularly for optical tags), one may print visible labels that identify or describe the identity of the optical surface 106 on the optical surface 106 itself. Care must be taken to ensure that the labels overlaid on the optical surface 106 do not interfere with the ability of the optical camera 102 to observe and interpret the markers 130. This may be achieved using techniques similar to those described for hiding the markers 130. For example, using a color that is transparent in the infrared portion of the spectrum but otherwise visible would allow the user to view the labels without obscuring the markers 130 from the camera 102.

Ultrasound Simulator

In the preferred embodiment, the optical probe 112 may be operatively connected to an external computing device 200 that runs a software ultrasound simulator similar, but not limited to, The SonoSim® Ultrasound Training Solution. An ultrasound simulator comprises at least one or more medical cases of interest, a user interface, and an image displaying an ultrasound slice 202 or other relevant medical imagery. The simulator may also display a virtual model of a patient, as well as a virtual model of the probe or syringe, visualizing the position and orientation of the physical optical probe 112 or syringe as held by the user.

The optical camera 102 (or a processor 108 connected to the optical camera 102) sends data through either a wired or wireless connection to the computing device 200 that runs the ultrasound simulator. The computing device 200 may either receive raw frame data directly from the optical camera 102 and run an algorithm to compute the position and orientation of the instrument 101, or it may receive the position and orientation of the instrument 101 already computed by the system through a processor 108 embedded in the optical probe 112 or syringe itself. The computing device 200 transmits the position and orientation of the optical probe 112 or syringe to the ultrasound simulator and, in turn, the ultrasound simulator updates the visualization to display an ultrasound image 202 that corresponds to the exact position and orientation of the optical probe 112 or syringe with respect to the optical surface 106 and the corresponding anatomy.

Principle of Operation

Figure 12A:
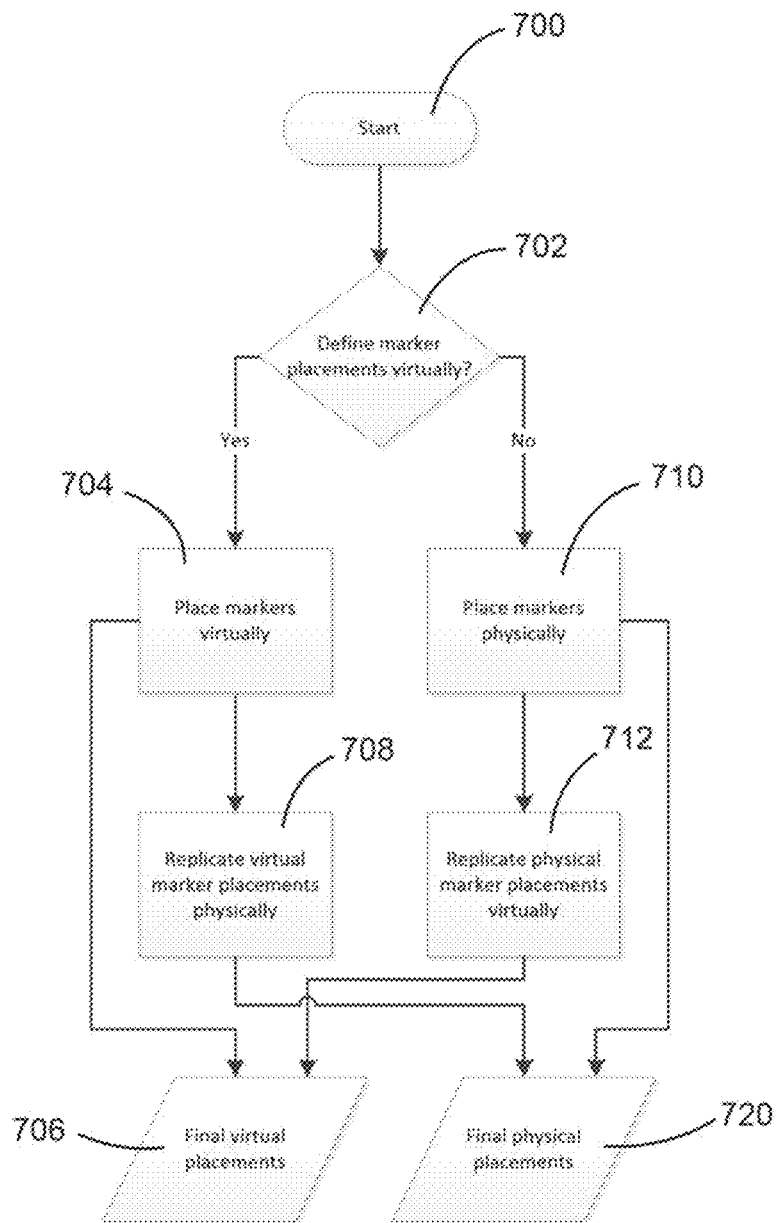
FIG. 12A shows a flow chart of two distinct surface construction techniques.
Figure 12B:
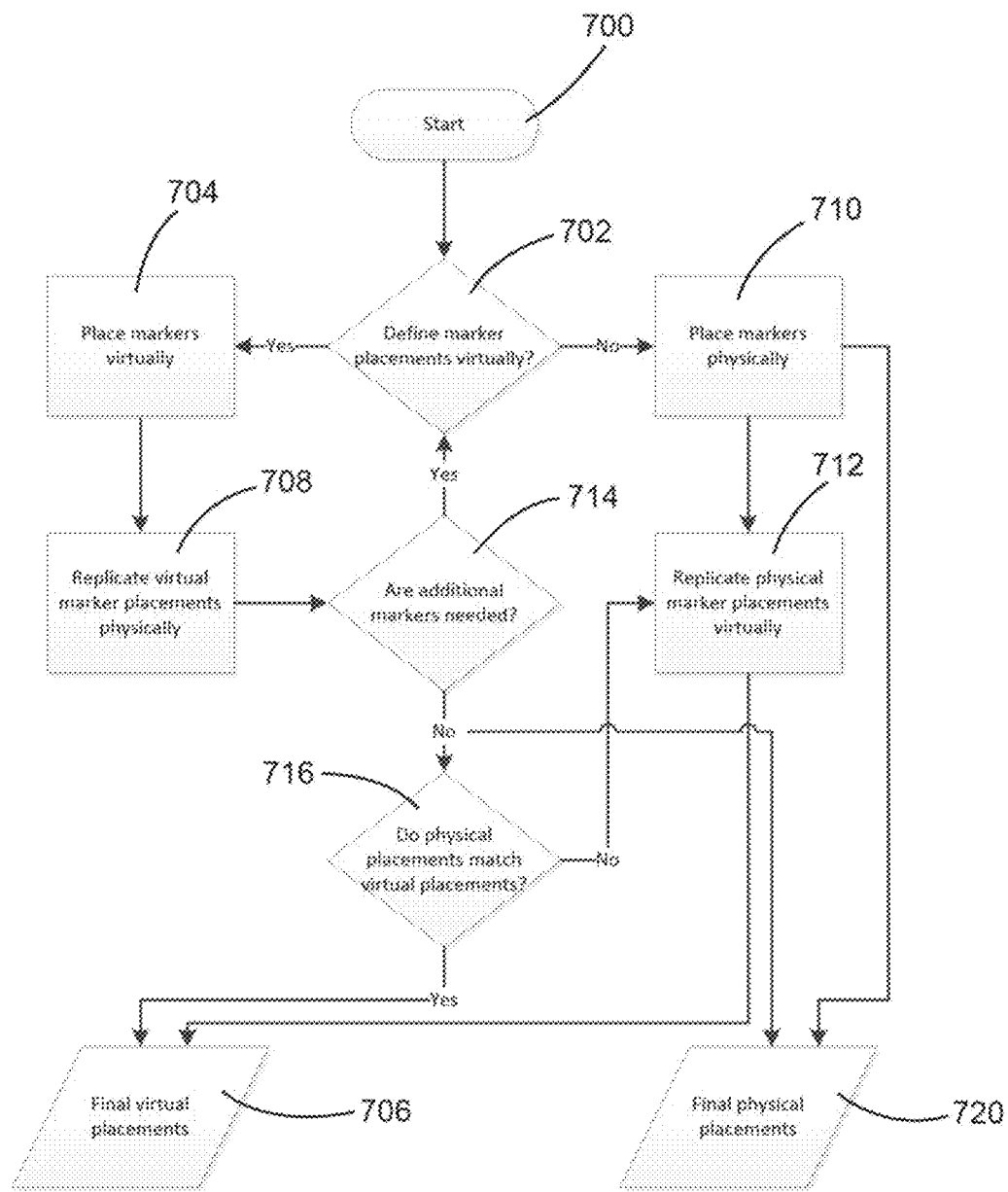
FIG. 12B shows a flow chart of surface construction techniques that allow for virtually placed markers to be augmented with physically placed markers.

With reference to FIGS. 12A-12B, prior to use, the user can start 700 the set up process for the markers 130. The user first determines whether the marker placement will be determined virtually 702. If so, then the user places the markers virtually 704 using a computer for example. Once the virtual markers are placed, the user can finalize the placements 706. Alternatively, before finalizing the virtual placements, the user can replicate the virtual markers with physical markers 708. Then the physical placements can be finalized 720.

Alternatively, at the step where the user determines whether the marker placement will be determined virtually 702, the user can select "no" and proceed to place the markers physically 710. The user can then finalize the final physical placements 720. Alternatively, prior to the finalization step 720, the user can replicate the physical marker placements virtually 712 and then finalize the virtual placement 706.

In some embodiments, additional markers may be needed. In such a situation, after virtual markers have been replicated physically, a determination can be made if additional markers are needed 714. If so, then the user repeats the process by determining whether the marker placement will be defined virtually 702. If not, then a check can be made to determine whether the physical placement matches the virtual placement 716. If so, then final virtual placements are made 706. If not, then the user can have the system replicate physical marker placements virtually 712, and then finalize virtual placements 706.

In the preferred embodiment, when the device is turned on, the optical camera 102 begins acquiring a continuous stream of images of its view through the viewing window 124. When the instrument 101 is placed adjacent (e.g. on or near) an optical surface 106 in the manner of scanning or performing a procedure, the images will contain observations of the markers 130. For each observation of the markers 130, the algorithm running on the processor 108 first identifies the pixels corresponding to the markers 130, thus ignoring confounding elements, such as glare, internal reflections, stains, and other undesirable occluders.

The algorithm rejects markers 130 that are partially or poorly visible. This may include removing markers 130 at the boundaries of the viewing window 124, which are likely to be partially occluded by the edge of the viewing window 124.

For each clearly visible marker 130, the algorithm uses the high contrast between black and white (or similarly distinguishable colors) regions to reliably identify the positions of the corners of each marker 130 in the image. Additional techniques that are well known to those skilled in the art can be used to further refine the estimated position of each corner beyond the resolution of a single pixel (i.e. sub-pixel accuracy). Knowledge of the camera 102 parameters combined with observations of how perspective has affected the corners of the markers 130 in the image allows the algorithm to uniquely determine the position and orientation of the camera 102 in 3D space with respect to the observed marker 130. By extension, knowledge of the position and orientation of the camera 102 can be used to determine the position and orientation of the probe 112 or syringe with respect to the marker 130.

In the embodiment of the syringe in which the camera 102 retracts relative to the enclosure 104, a marker on the inside of the enclosure 104 will be visible to the camera 102. Similar to how the processor 108 can determine the position and orientations of the camera 102 relative to a marker 130 on the surface 106, the processor 108 can determine the position and orientation of the camera 102 relative to a marker 130 on the inside of the enclosure 104. The processor 108 can then combine these two transformations (camera 108 position and orientation relative to the surface 106 marker 130 and camera 108 position and orientation relative to the enclosure 104) to determine the transformation between the enclosure 104 and the surface 106 marker 130, thus determining the position and orientation of the optical syringe with respect to the marker 130.

The algorithm analyzes the pattern of pixels within the individual marker 130 to decode the numerical value encoded within it in a manner similar QR codes or bar codes as is known to those skilled in the art. The algorithm references the numerical value through an algorithmic mapping or internal look-up table to determine how the observed marker 130 is positioned and oriented on the surface 106. This information allows the algorithm to fully resolve the position and orientation of the instrument 101 with respect to the surface 106.

In the preferred embodiment, the processor 108 transmits the numerical value of the given optical surface 106 to the ultrasound simulator, which uses this information to identify which location on the body is being scanned and to load a corresponding ultrasound volume accordingly. Knowledge of the position and orientation of the instrument 101 relative to the optical surface 106, the identifier of the optical surface 106 being scanned, and the position and orientation of the identified optical surface 106 with respect to the body, allow the ultrasound simulator to compute and visualize an ultrasound image 202 that emulates what the user would see if they were scanning a real patient by placing a real probe or syringe at the corresponding position and orientation.

In most cases, the instrument can view more than one marker 130 in a single image. The algorithm can exploit this redundancy to achieve more accurate estimates and make the tracking more robust to cases where a subset of markers 130 may be poorly visible. This can be accomplished in a few ways, including but not limited to:

Estimating the position and orientation of the instrument 101 for each visible marker 130 individually and then averaging the results.

Exploiting prior knowledge about the geometric arrangement of the markers 130 on the surface 106 to identify a single, more robust position and orientation estimate. For example, knowledge of the positions of each marker 130 corner can allow an algorithm to compute the camera 102 position and orientation without knowledge of which marker 130 corresponds to which corner. Algorithms for solving such computations can be found in common computer vision literature and libraries, such as OpenCV (e.g. the solvePnP and solvePnPRansac functions).

Extensions

The base invention described thus far can be improved with various extensions to add additional behavior or to leverage other technologies.

Extension: Compression

In one embodiment of the probe 112, the head 122 is designed in such a way as to allow the probe 112 to determine compression, an important aspect of ultrasound diagnosis. Ultrasound scans often do not provide enough visual cues to differentiate certain types of anatomical structures that have distinct functions but similar appearances, such as veins and arteries. One diagnostic technique commonly used by practitioners involves pressing the probe against the body in order to observe how the underlying tissues deform under compression. Different anatomical structures react differently due to their distinct elastic properties and these distinctions allow clinicians to reliably differentiate the corresponding tissues. Therefore, a solution that can emulate this aspect of ultrasound diagnosis is desirable. The present invention allows for simulation of compression through the ability of the algorithm to perform full 6-DOF tracking of the instrument.

Figure 10A:
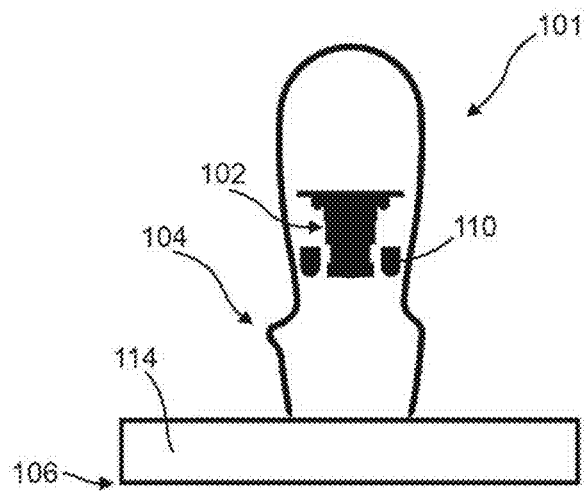
FIGS. 10A-10B show embodiments of a probe demonstrating different means of identifying compression.
Figure 10B:
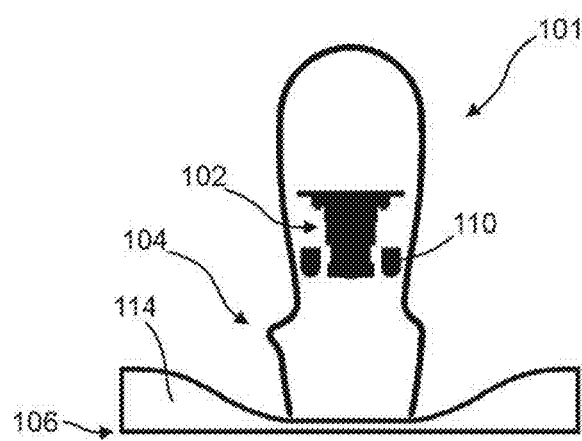

In some embodiments, a compressible layer 114 may be placed over an optical surface 106 (see FIGS. 10A and 10B). The compressible layer 114 may be a transparent material. If the calculated distance between the head 122 of the optical probe 112 and the optical surface 106 is equal to the nominal thickness of the transparent material, the algorithm determines that the optical probe 112 is making contact with the surface 106 without compressing it. If, instead, the distance between the head 122 of the optical probe 112 and the optical surface 106 is less than the nominal thickness of the transparent material, it must be in a compressed state and the amount of compression is determined by the distance between the head 122 of the optical probe 112 and the optical surface 106. One can choose the elasticity of the compressible layer 114 to provide an amount of resistance that mimics that of a real body.

Figure 11A:
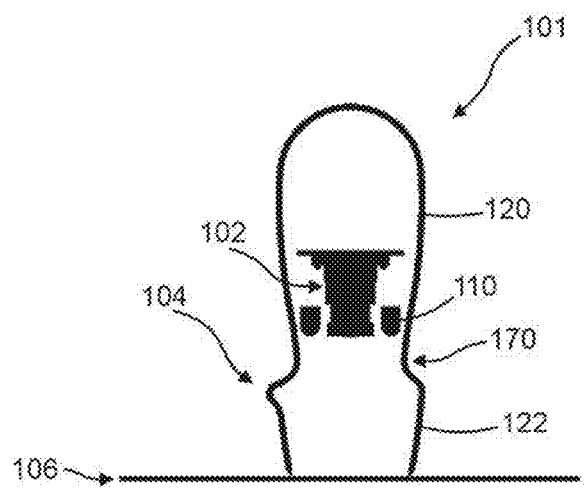
FIGS. 11A-11B show embodiments of a probe demonstrating different means of identifying compression.
Figure 11B:
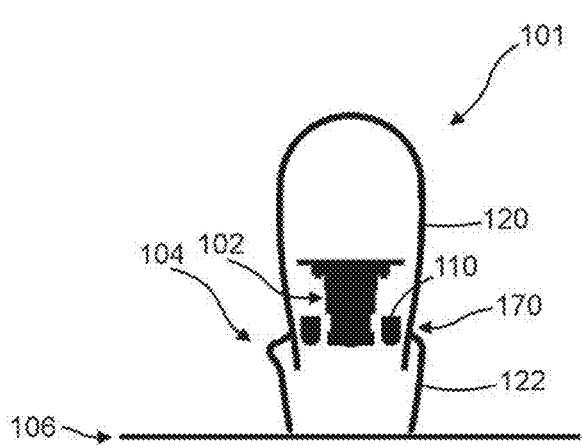

In another embodiment, a special mechanical slide assembly 170 may allow the head 122 of the optical probe 112 to move inward and closer to the camera 102 when pressure is applied to it (see FIGS. 11A-11B). The mechanical slide 170 uses a spring or similar component to restore the position of the head 122 to its nominal position when pressure is removed. Alternatively, a compressible layer or rim may be applied to the head 122 of the optical probe 112. If the calculated distance between the optical camera 102 and the optical surface 106 is equal to the nominal distance between the optical camera 102 and the head 122 of the optical probe 112, the algorithm determines that the optical probe 112 is making contact with the surface 106 without compressing it. If, instead, the distance between the optical camera 102 and the optical surface 106 is less than the nominal distance between the optical camera 102 and the head 122 of the optical probe 112, it must be in a compressed state and the amount of compression is determined by the distance between the optical camera 102 and the optical surface 106. One can choose the elasticity of the spring or compressible layer to provide an amount of resistance that mimics that of a real body.

Regardless of the manner in which the amount of compression is obtained and computed, the processor 108 transmits the amount of compression to the computing device 200 and the ultrasound simulator will respond accordingly by visualizing ultrasound images 202 at the corresponding level of compression.

Extension: Markers

The present invention can be extended using other optical tracking techniques known to those skilled in the art. For example, hierarchical or recursive markers 130 could provide more robust tracking at different distances. Instead of markers 130 with distinctly arranged pixels, different types of visual data could be used. For example, the markers 130 could be replaced by a genetic photograph as long as it contains dense, recognizable features. These could be applied as fine splatter patterns, and made to resemble skin blemishes or freckles so as not to look unnatural. Finally, a solution based on simultaneous localization and mapping (SLAM) could also achieve outcomes consistent with the spirit of the invention.

Extension: Additional Sensors

To improve tracking robustness, the present invention can be coupled with additional sensors. A gyroscope, accelerometer, and magnetometer could provide additional tracking information when few or no markers 130 are visible and at a higher rate than what is generally possible with a low cost optical camera 102 and processor 108. Pressure sensors (e.g. resistive or capacitive strain gauges, load cells, etc.) could provide a substitute for the compression solution. A light sensor could be included to allow the device to control the amount of light provided by the light source 110 in order to produce consistent lighting in different environments and at different distances from the optical surface 106. A proximity sensor could also be included to help the device control the amount of light provided by the light source 110, or alternately to help with automatic focusing of the camera 102.

Extension: Interface

While the main purpose of our invention is to simulate medical scanning and needle guided procedures, the techniques presented can also be used to perform other tasks, such as software interface control. For example, certain optical surfaces 106 may be designated to represent standard computer commands such as "save" or "exit," or proprietary commands specific to a piece of software. In such an embodiment, placing an optical instrument on one of these surfaces would trigger the software to perform the corresponding command. This embodiment can work seamlessly with the main embodiment as well, such as using the optical probe 112 for scanning on one optical surface 106, then placing it on another surface 106 to perform a task such as switching to another anatomical dataset. An optical surface 106 could also be used for more advanced interface control, such as moving a cursor.

Alternative Embodiments

Figure 3A:
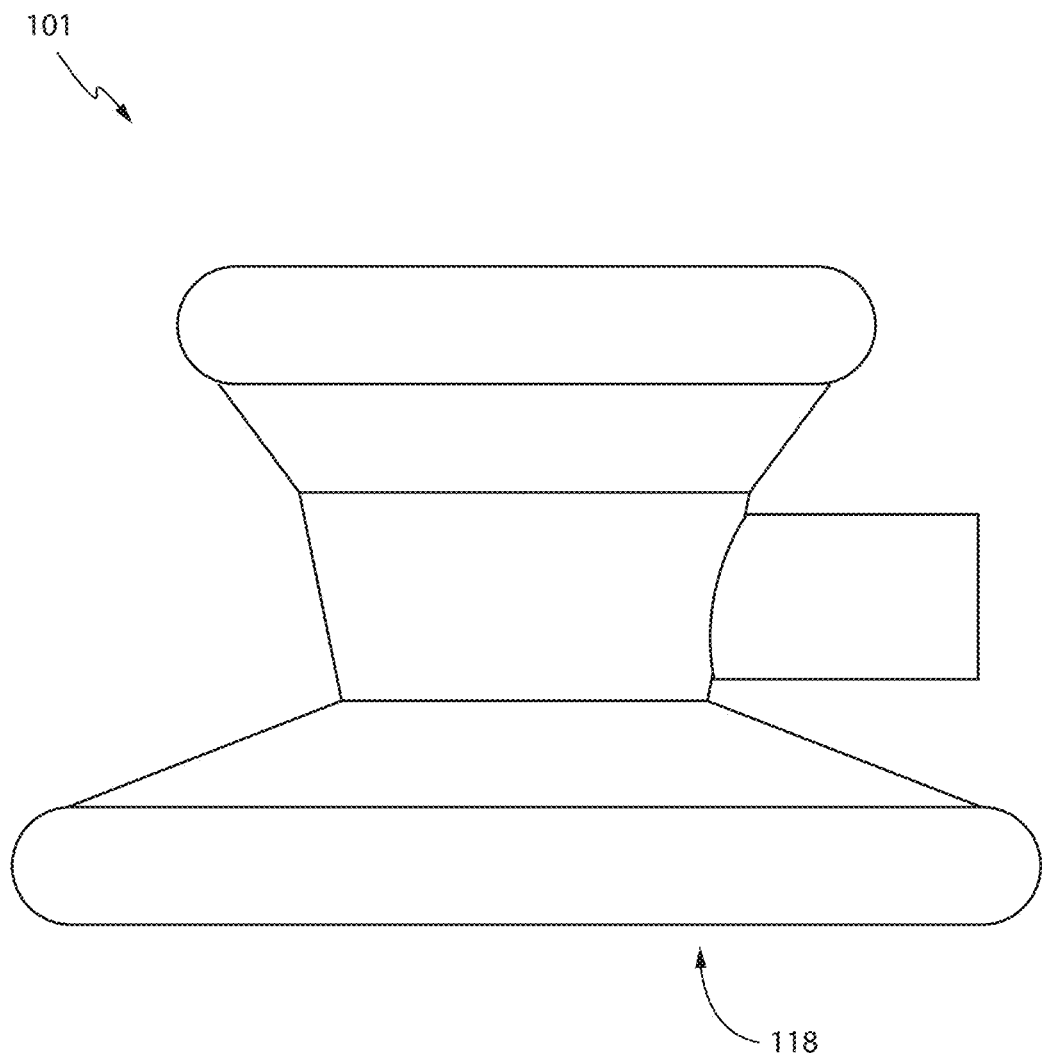
FIG. 3A shows an embodiment of a stethoscope.
Figure 3B:
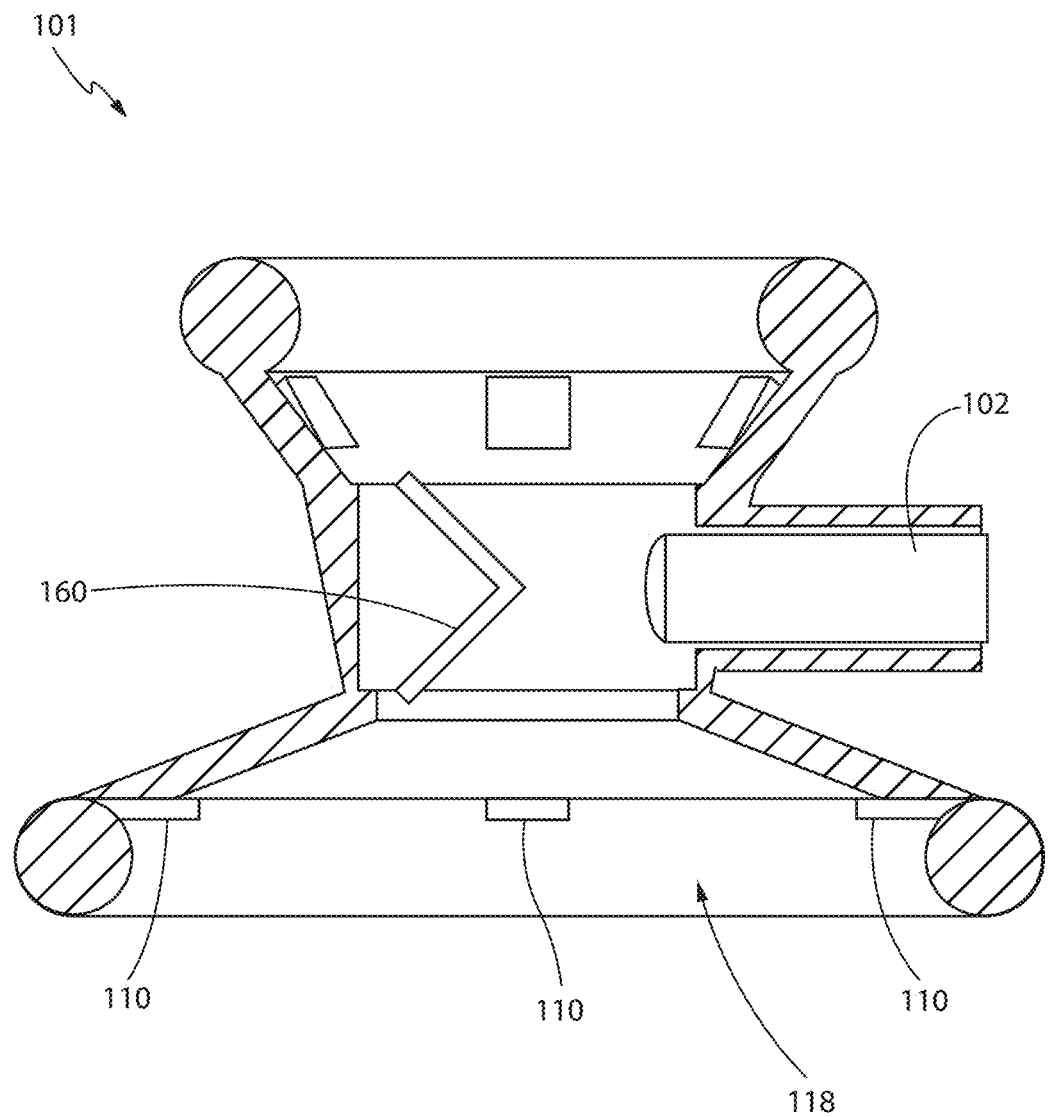
FIG. 3B shows an embodiment of the stethoscope shown in FIG. 3A in cross-section to reveal internal components.

While the invention as presented here covers applications to a mock ultrasound probe 112 and syringe, the same concepts can be applied to track other medical instruments, such as a stethoscope (see FIG. 3) or scalpel, or even general purpose instruments such as a joystick or pen.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

The invention claimed is:

1. A system for training a user to use a medical ultrasound device, the system comprising:
   a) an instrument that mimics the medical ultrasound device, the instrument comprising:
      i) an enclosure defining an opening; and
      ii) a camera housed inside the enclosure and configured to view out the opening, the camera having a fixed focus;
   b) a computing device operatively connected to the instrument to receive information from the camera;
   c) a plurality of markers, each marker being comprised of a grid having 6 squares by 6 squares, the marker having a dimension of approximately 4 mm by 4 mm, each marker encoding a unique numerical value, and having a position, an orientation, a size, a shape, and a spacing relative to each other, wherein the size, the shape, and the spacing relative to each other are known by the computing device in advance, and can be associated with the encoded numeric value by using an algorithmic mapping or a look-up table, wherein each marker comprises a visibly opaque but infrared transparent layer, wherein the plurality of markers are placed adjacent to each other to form an optical tag having a dimension of approximately 7 cm by 7 cm, wherein the optical tag encodes a specific body region;
   d) a surface upon which the plurality of markers are attached, the surface selected from a group consisting of a flat surface and a three-dimensional mode;

e) a light source configured to illuminate a set of markers from the plurality of markers that are visible to the camera through the opening; and f) a simulator executable by the computing device to run a simulation of a procedure in real time, wherein the set of markers viewable by the camera through the opening contain information for generating an ultrasound image directly from the set of markers viewable by the camera.

* * * * *